(12) United States Patent
Hannema et al.

(10) Patent No.: US 12,318,302 B2
(45) Date of Patent: Jun. 3, 2025

(54) INTERSPINOUS IMPLANT AND ASSOCIATED IMPLANTATION ANCILLARY

(71) Applicant: INNOSPINA SARL, Courroux (CH)

(72) Inventors: Gwenael Loïc Hannema, Zurich (CH); Jacques Samani, Saint Barthelemy (FR); Dominique Constant Beuchat, Chatillon (CH)

( * ) Notice: Subject to any disclaimer, the term of this patent is extended or adjusted under 35 U.S.C. 154(b) by 0 days.

(21) Appl. No.: 17/626,060

(22) PCT Filed: Jul. 7, 2020

(86) PCT No.: PCT/EP2020/069143
§ 371 (c)(1),
(2) Date: Jan. 10, 2022

(87) PCT Pub. No.: WO2021/000507
PCT Pub. Date: Jan. 14, 2021

(65) Prior Publication Data
US 2022/0249243 A1     Aug. 11, 2022

(30) Foreign Application Priority Data

Jul. 8, 2019   (FR) ...................................... 1907608
Jul. 8, 2019   (FR) ...................................... 1907609

(51) Int. Cl.
*A61F 2/44*      (2006.01)
*A61F 2/46*      (2006.01)
*A61F 2/30*      (2006.01)

(52) U.S. Cl.
CPC .......... *A61F 2/4405* (2013.01); *A61F 2/4611* (2013.01); *A61F 2002/30131* (2013.01);
(Continued)

(58) Field of Classification Search
CPC .... A61F 2/4405; A61F 2/4465; A61F 2/4455; A61B 17/7062; A61B 17/7068
(Continued)

(56) References Cited

U.S. PATENT DOCUMENTS 8,172,878 B2 *  5/2012  Yue ..................... A61B 17/7065
                                                   606/248
8,292,958 B1 * 10/2012  Bruffey ................. A61F 2/4611
                                                   606/247
(Continued)

FOREIGN PATENT DOCUMENTS

EP   3294166 A1   3/2018
FR   3003159 A1   9/2014

OTHER PUBLICATIONS

International Search Report issued Mar. 1, 2021 re: Application No. PCT/EP2020/069143, pp. 1-4.

*Primary Examiner* — Eduardo C Robert
*Assistant Examiner* — Christina Negrelli-Rodriguez

(57) ABSTRACT

An interspinous implant includes an implant body extending along a longitudinal axis and having, in succession: a rear part having a rear end, and a central part shaped to extend between two spinous processes of two adjacent vertebrae, the central part extending the rear part. The implant further includes a front part extending the central part, in the opposite direction from the rear part, and tapering down to a front end of streamlined shape. The implant body has an anterior face intended to face toward the vertebrae and in which there is formed an anterior groove of curvilinear shape, extending from the rear end as far as the front end in a curvilinear direction, to accept at least a portion of an implantation prong of an implantation ancillary.

13 Claims, 15 Drawing Sheets

(52) U.S. Cl.
CPC ............... *A61F 2002/30841* (2013.01); *A61F 2002/4627* (2013.01)

(58) Field of Classification Search
USPC ........................................................ 606/248
See application file for complete search history.

(56) References Cited

U.S. PATENT DOCUMENTS

| | | | |
|---|---|---|---|
| 8,361,116 B2 * | 1/2013 | Edmond | A61B 17/7068 |
| | | | 606/248 |
| 8,672,977 B2 * | 3/2014 | Siegal | A61B 17/7065 |
| | | | 606/249 |
| 9,101,409 B2 * | 8/2015 | Nishida | A61B 17/7062 |
| 2003/0135275 A1 * | 7/2003 | Garcia | A61B 17/1671 |
| | | | 623/17.11 |
| 2004/0225361 A1 * | 11/2004 | Glenn | A61F 2/442 |
| | | | 623/17.12 |
| 2005/0055031 A1 | 3/2005 | Lim | |
| 2008/0082172 A1 * | 4/2008 | Jackson | A61B 17/7062 |
| | | | 606/139 |
| 2011/0009969 A1 | 1/2011 | Puno | |
| 2012/0226313 A1 | 9/2012 | Pace | |
| 2012/0265246 A1 * | 10/2012 | Yue | A61B 17/7065 |
| | | | 606/249 |
| 2013/0190820 A1 | 7/2013 | Siegfried et al. | |
| 2016/0242824 A1 * | 8/2016 | Kirschman | A61B 17/7068 |

* cited by examiner

[Fig. 1]
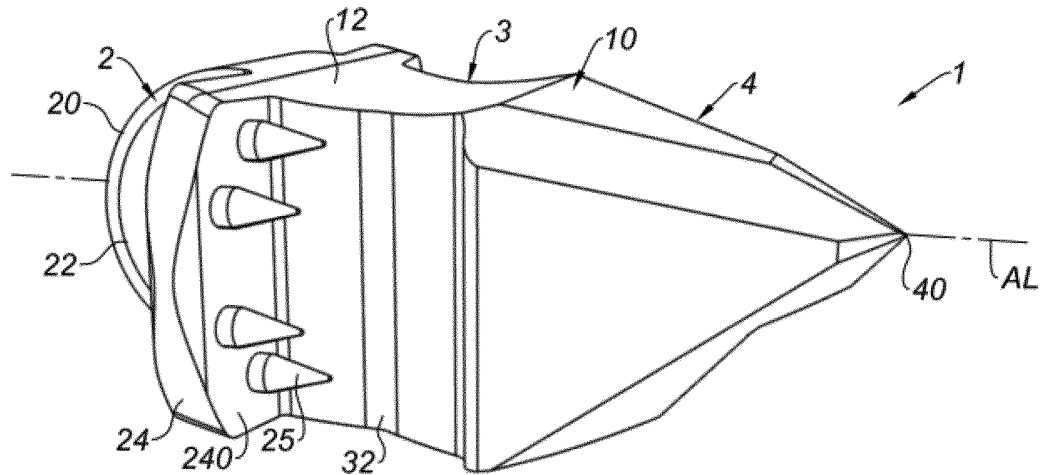
[Fig. 2]
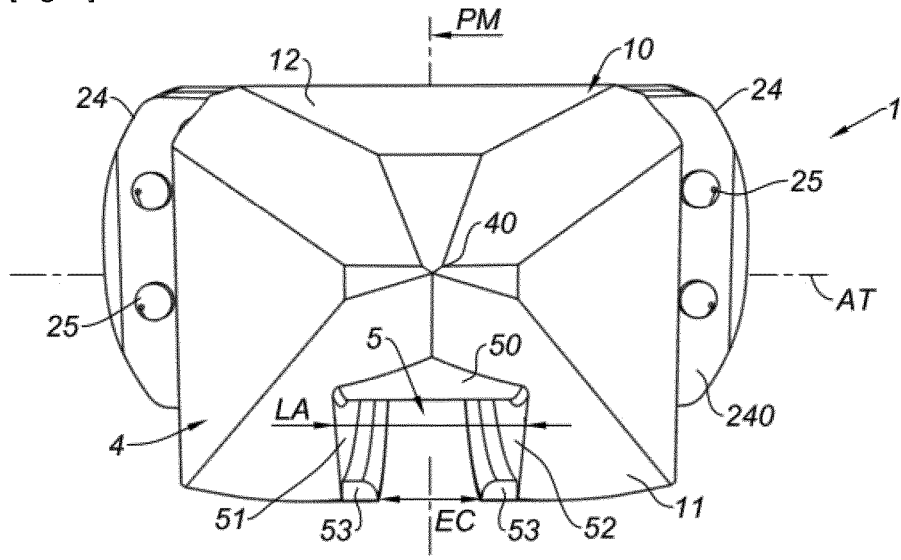
[Fig. 3]
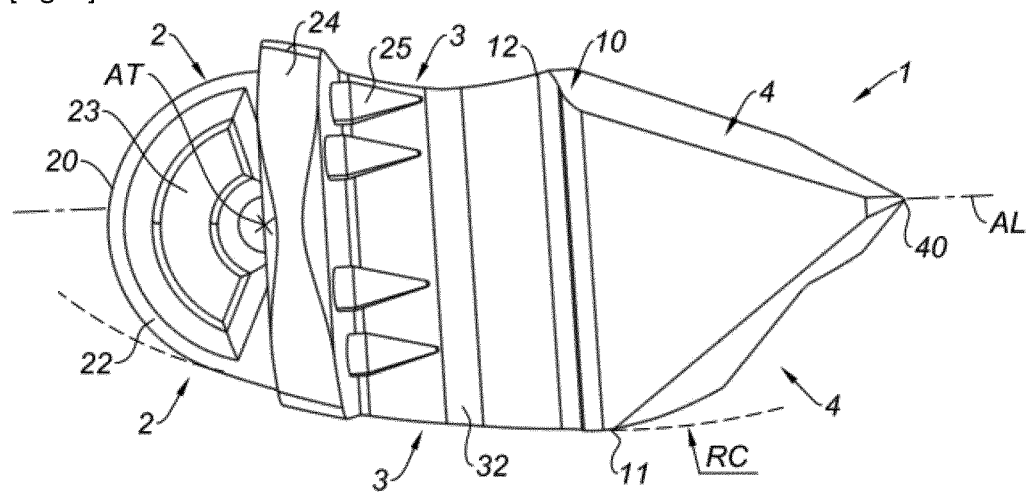

[Fig. 4]
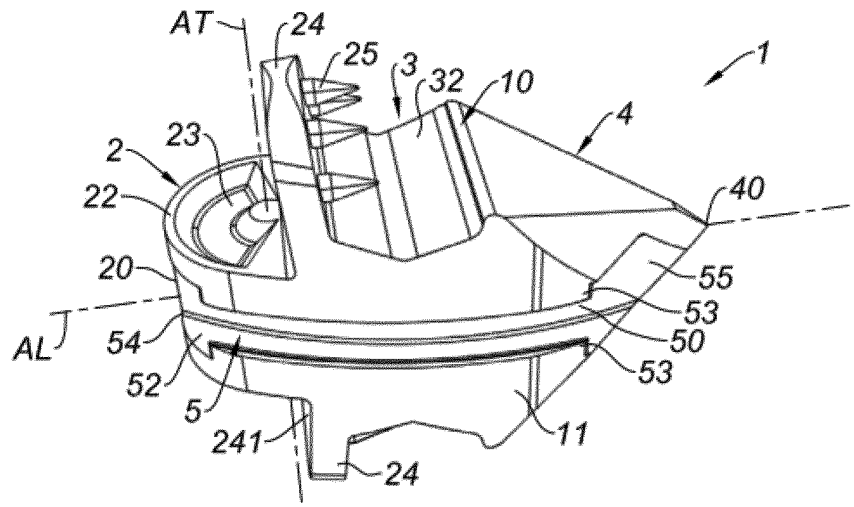
[Fig. 5]
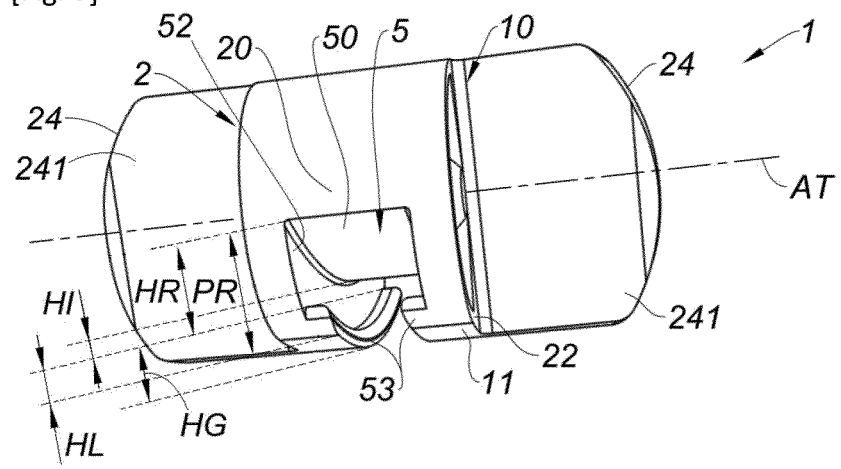
[Fig. 6]
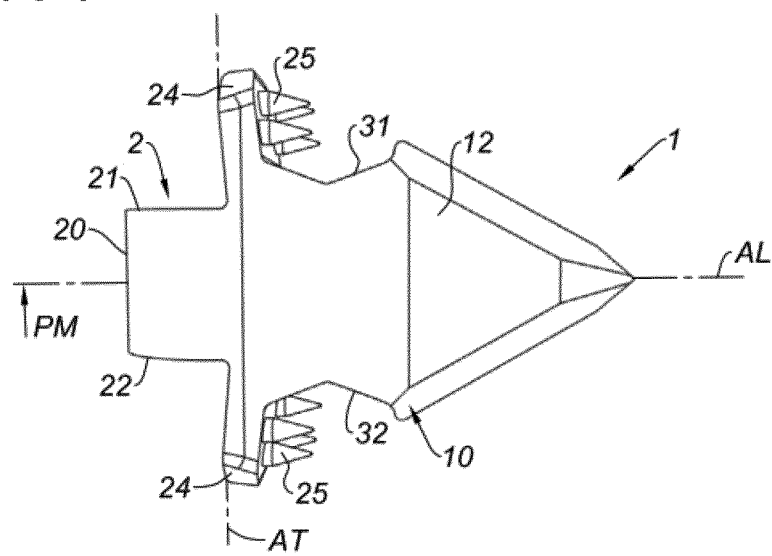

[Fig. 7]
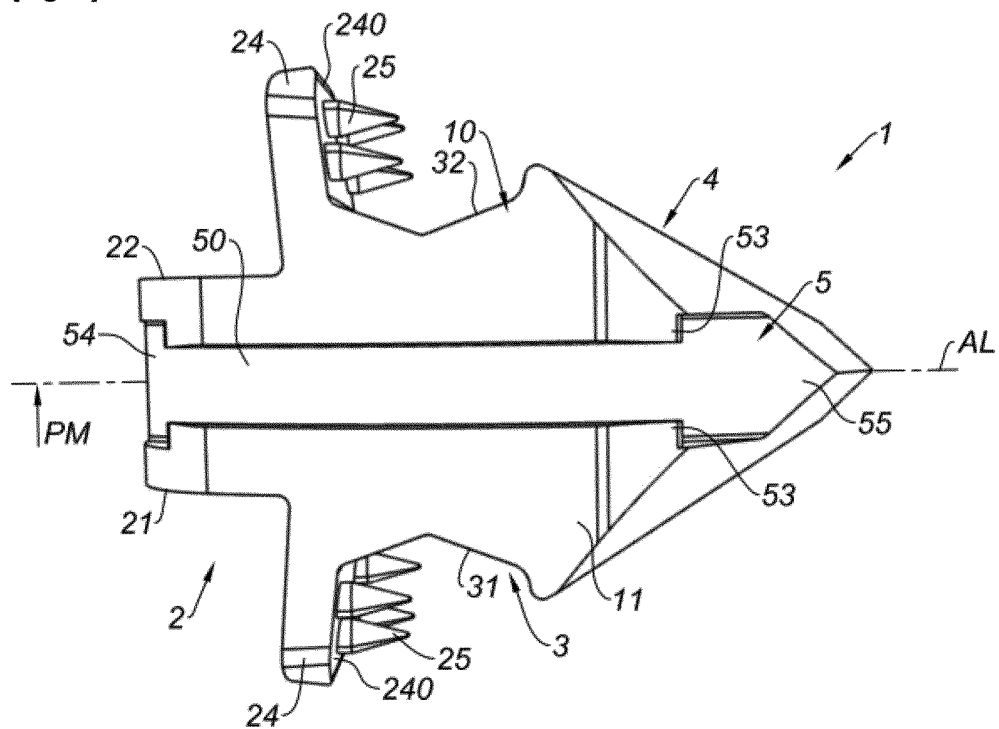
[Fig. 8]
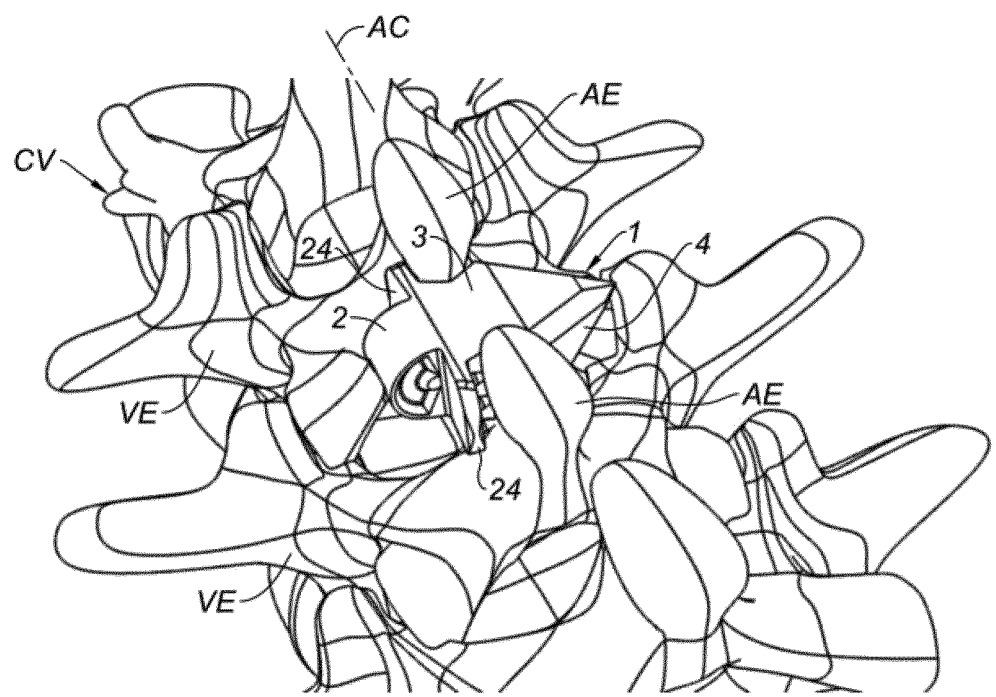

[Fig. 9]
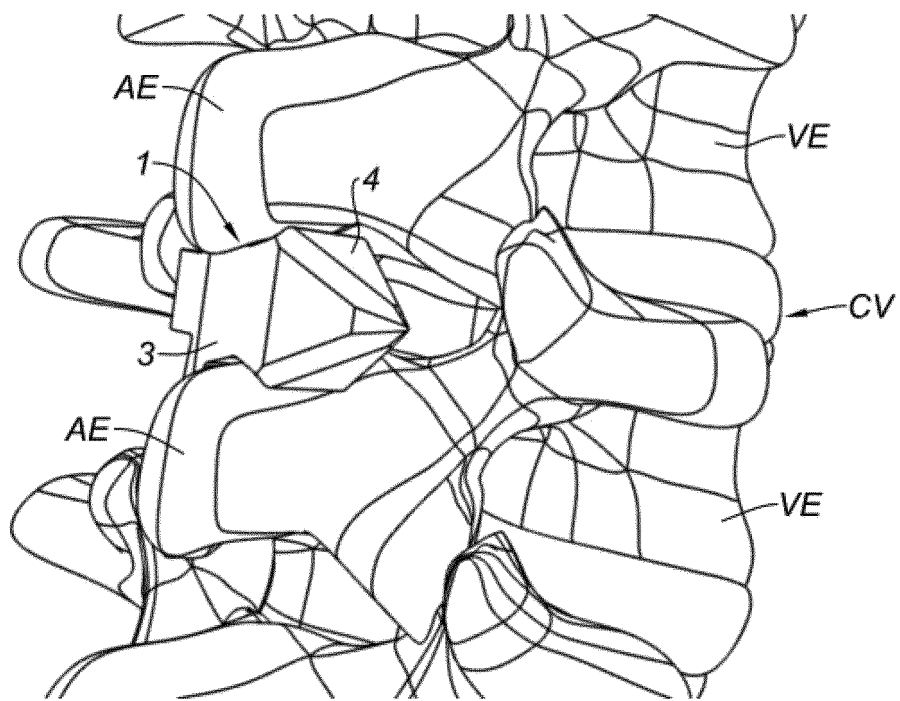
[Fig. 10]
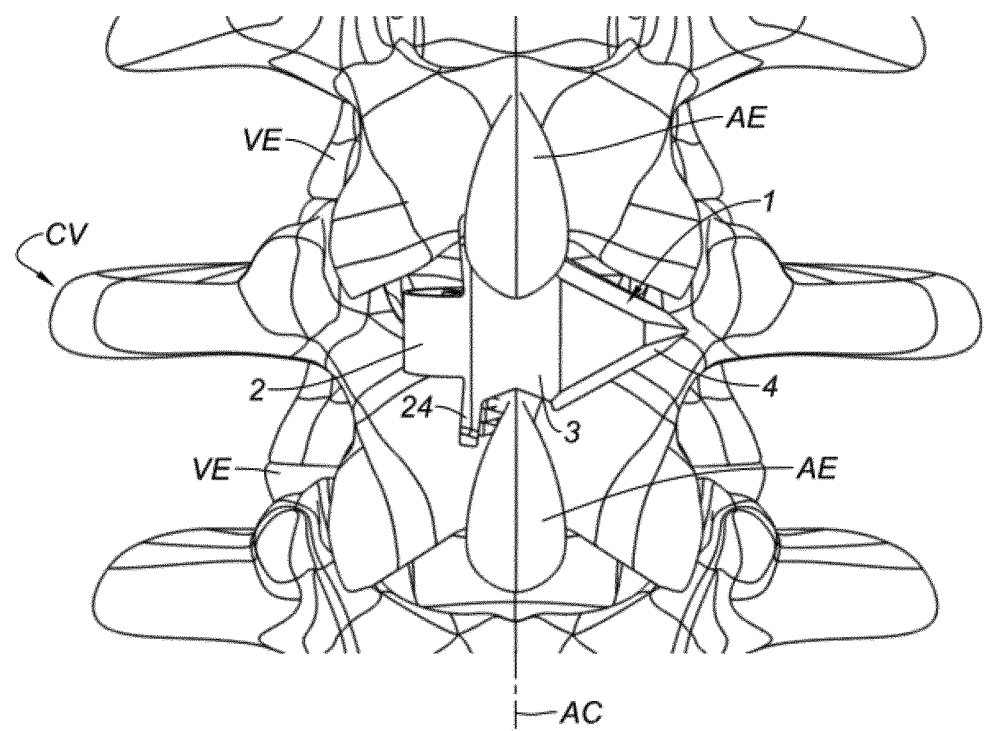

[Fig. 11]
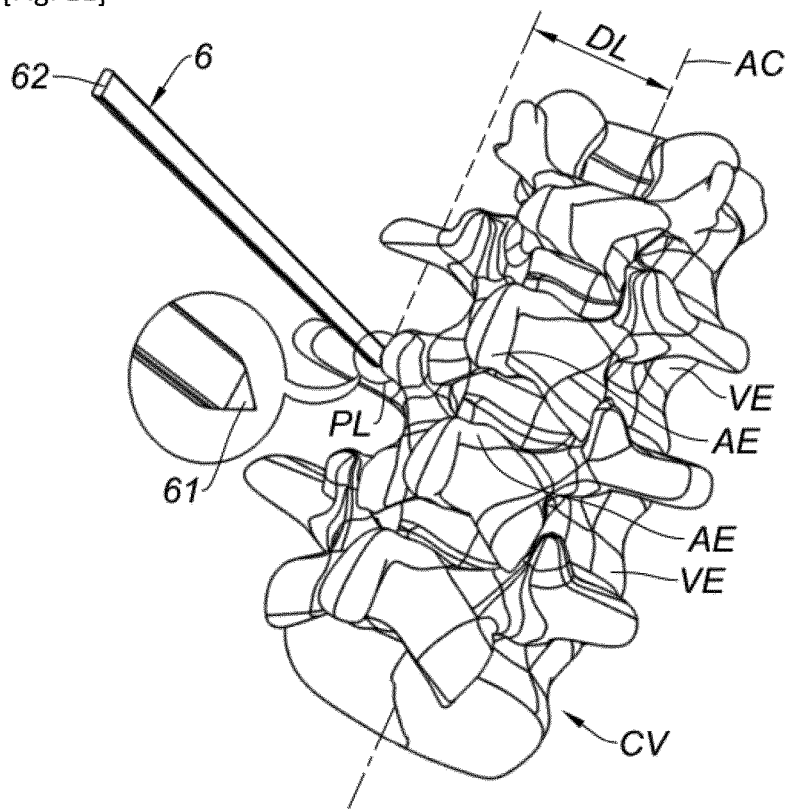
[Fig. 12]
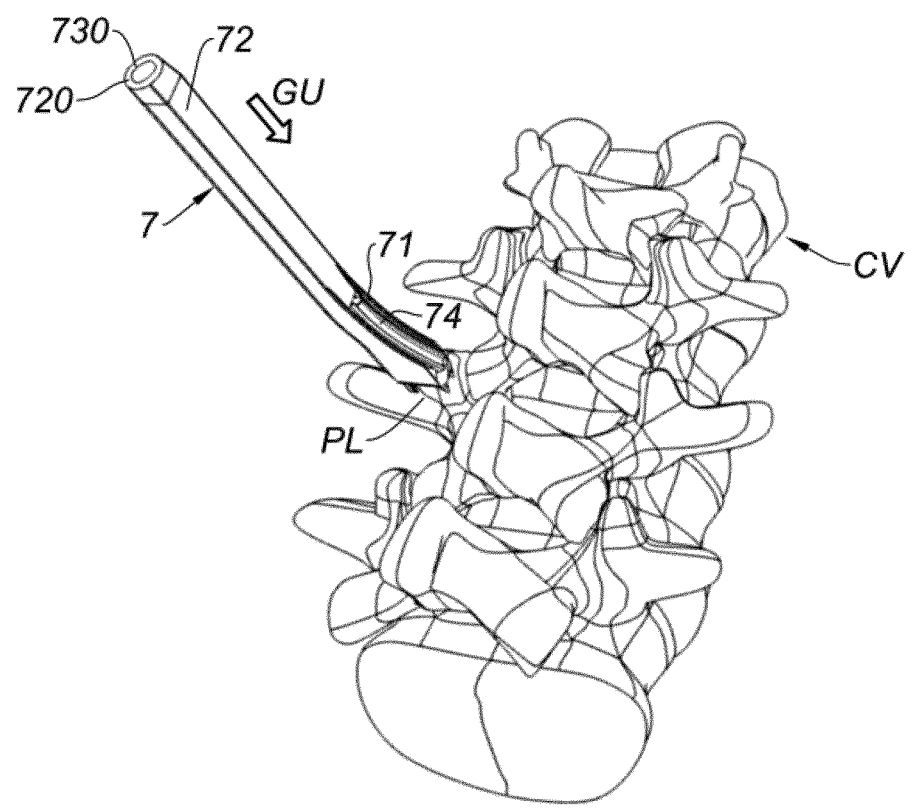

[Fig. 13]
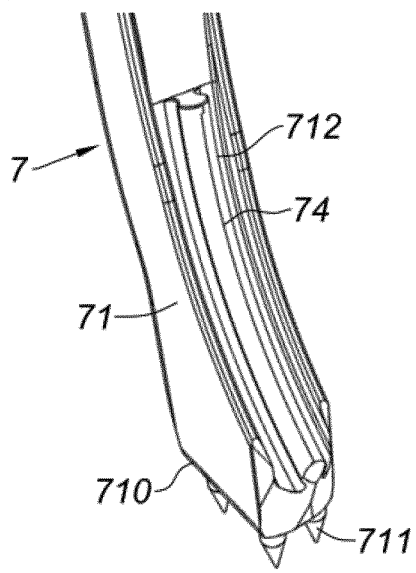
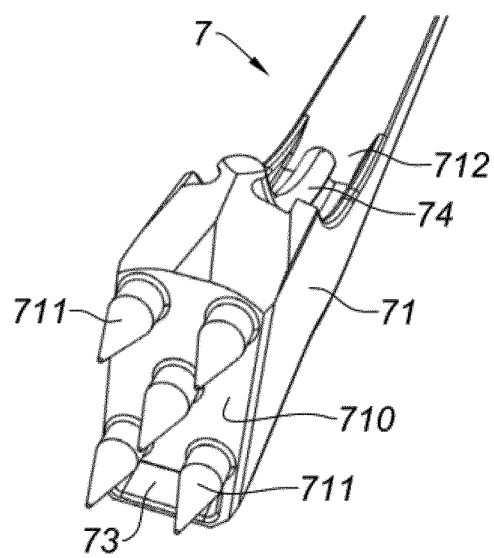
[Fig. 14]
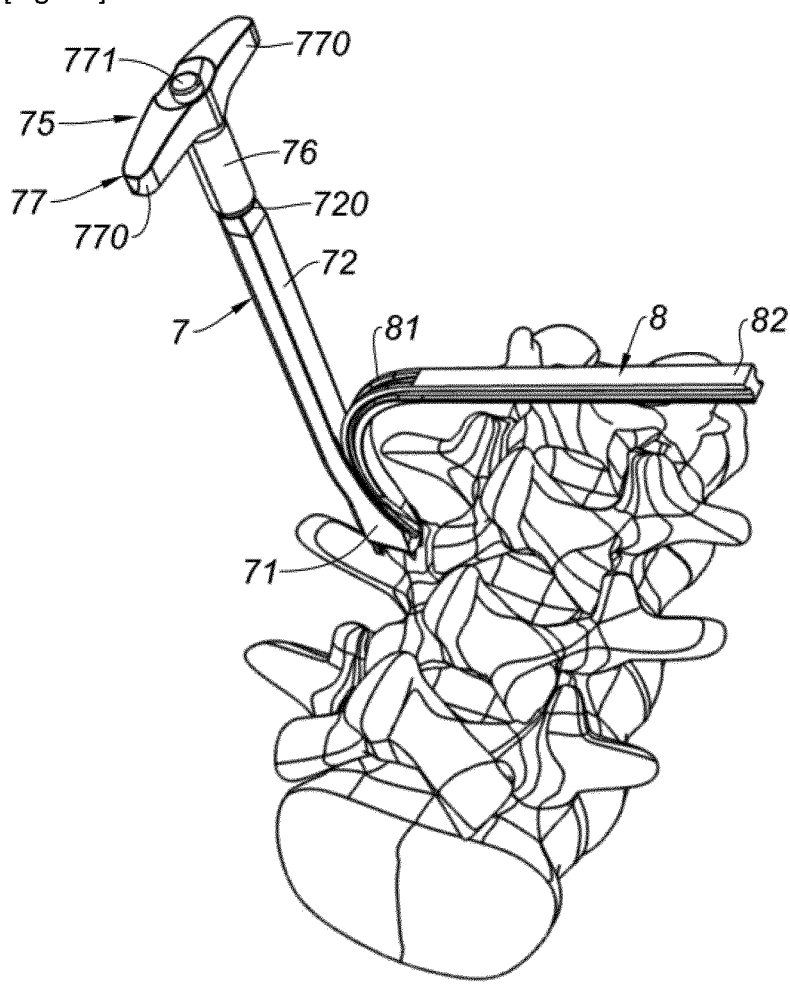

[Fig. 15]
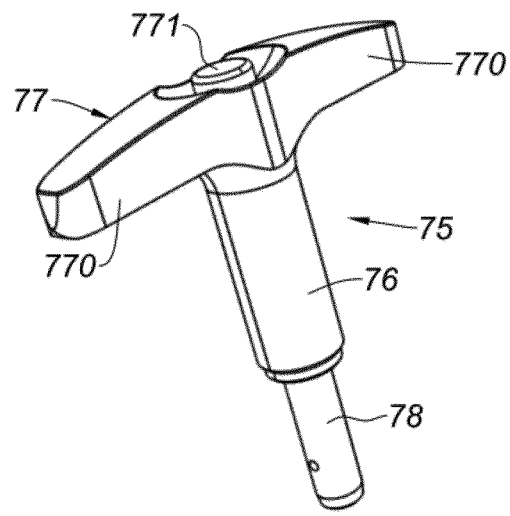
[Fig. 16]
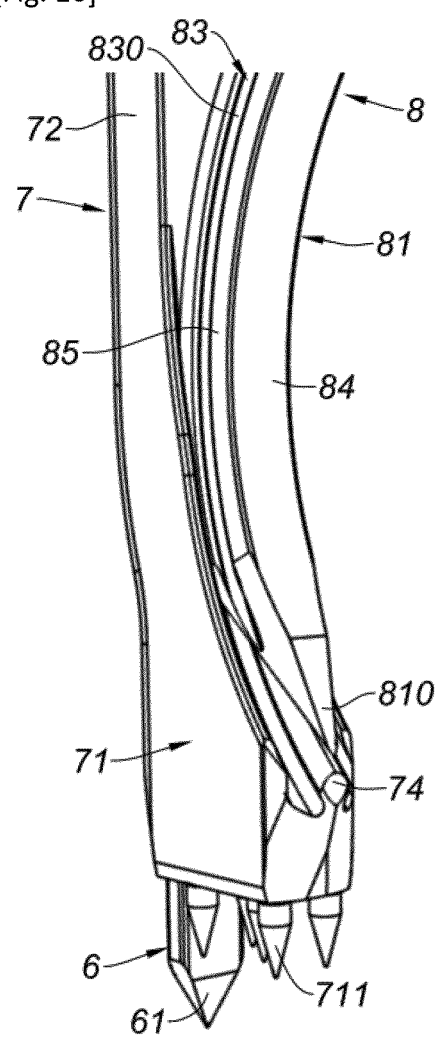

[Fig. 17]
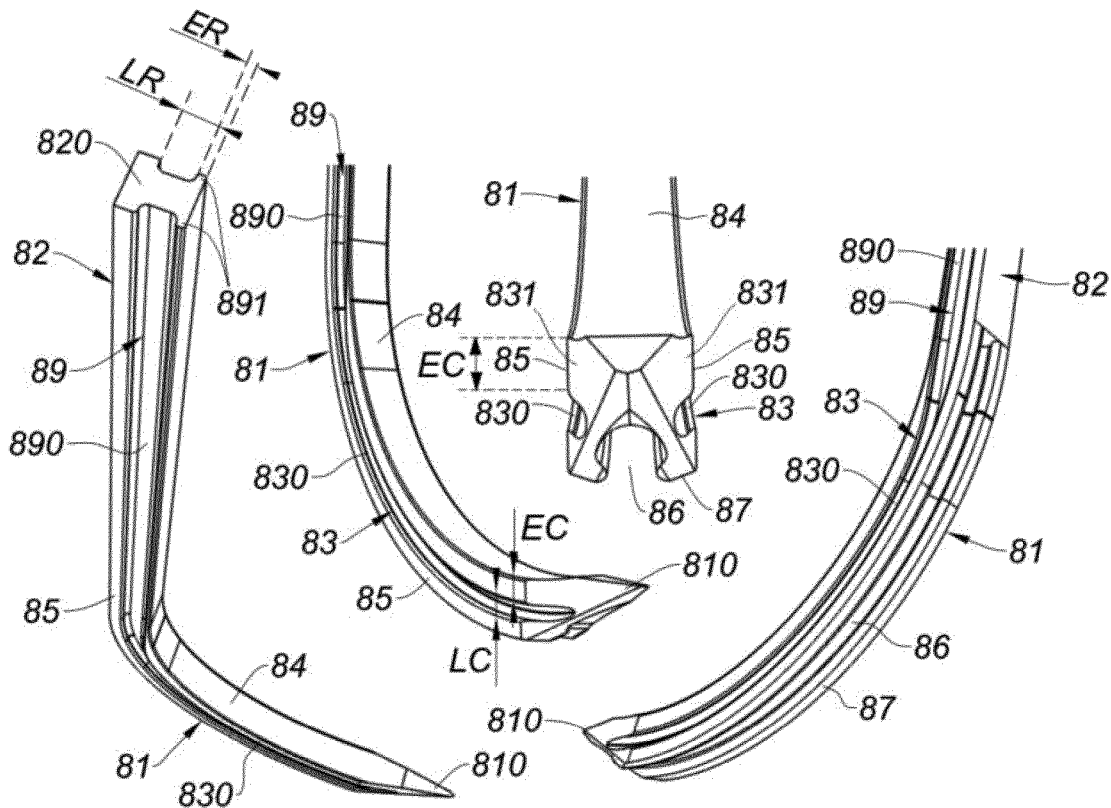
[Fig. 18]
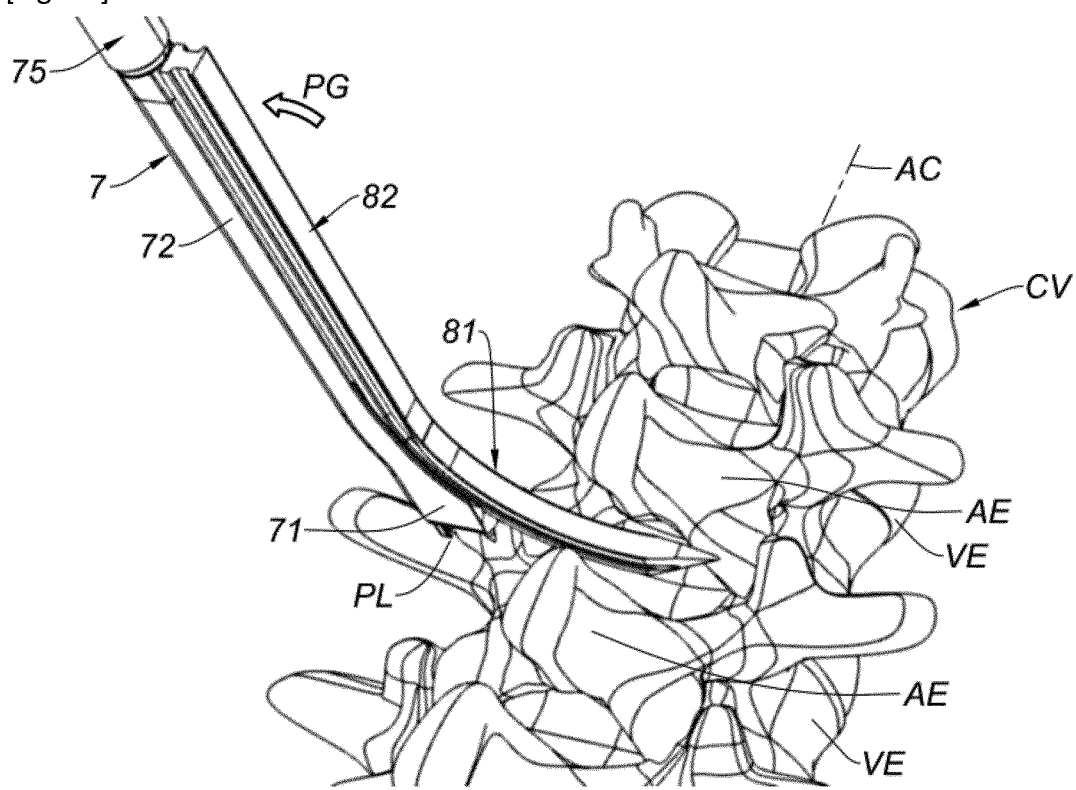

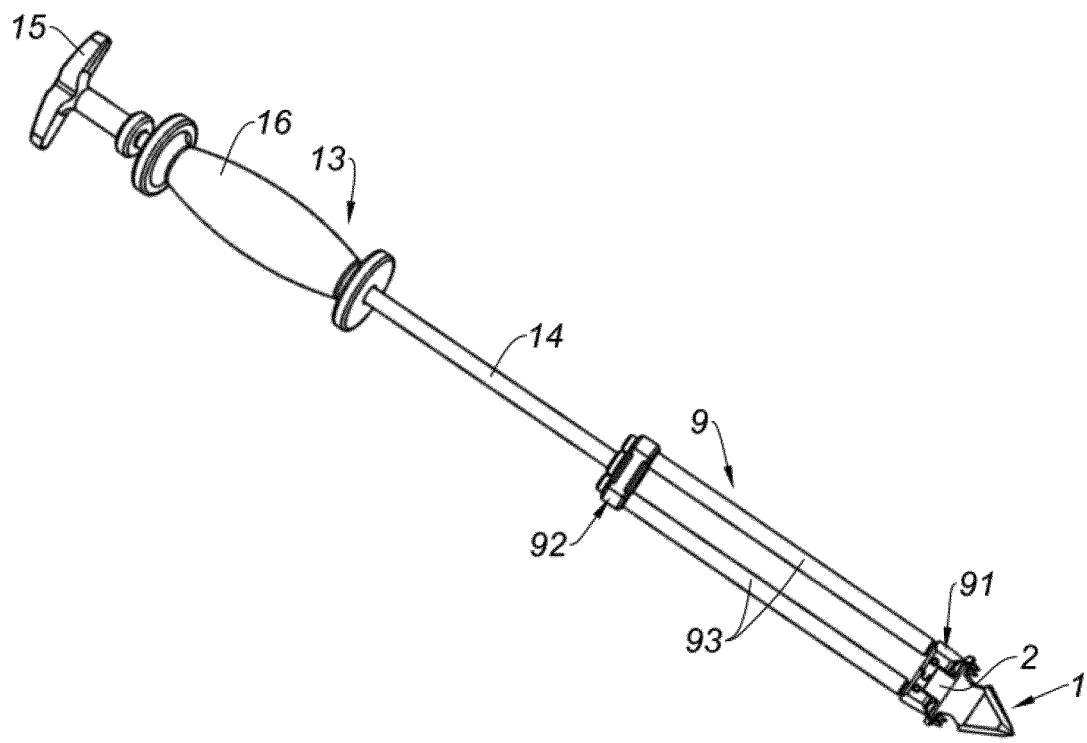
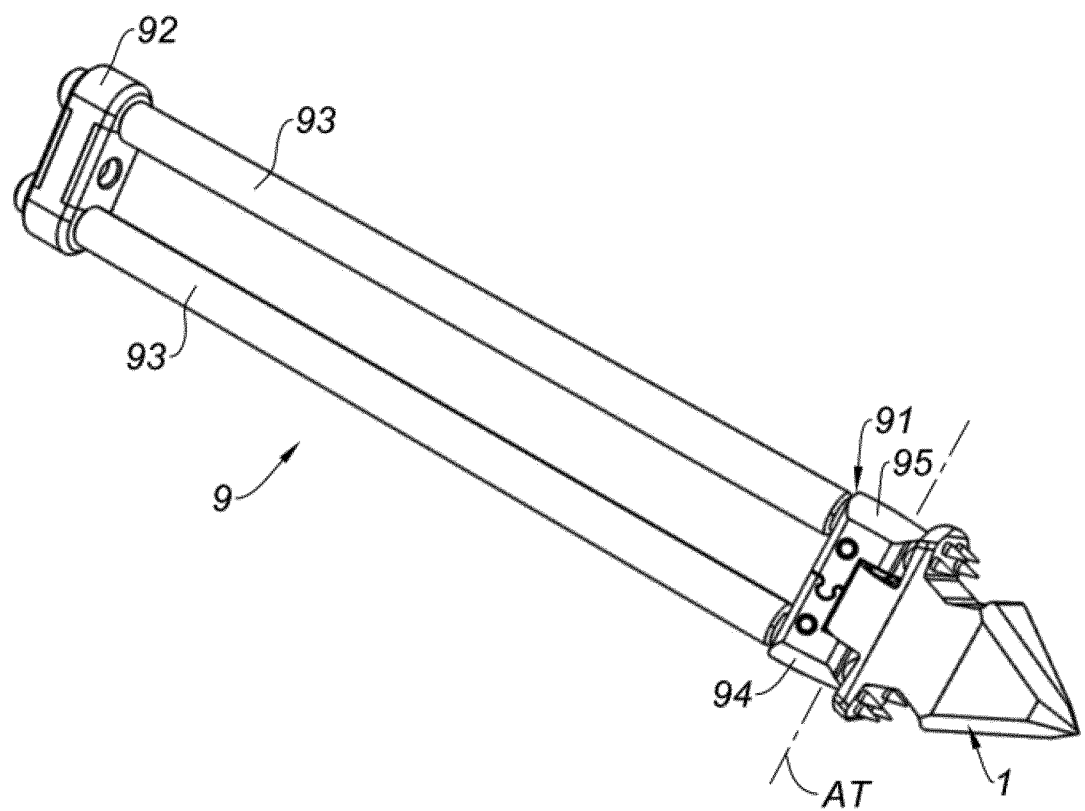

[Fig. 21]
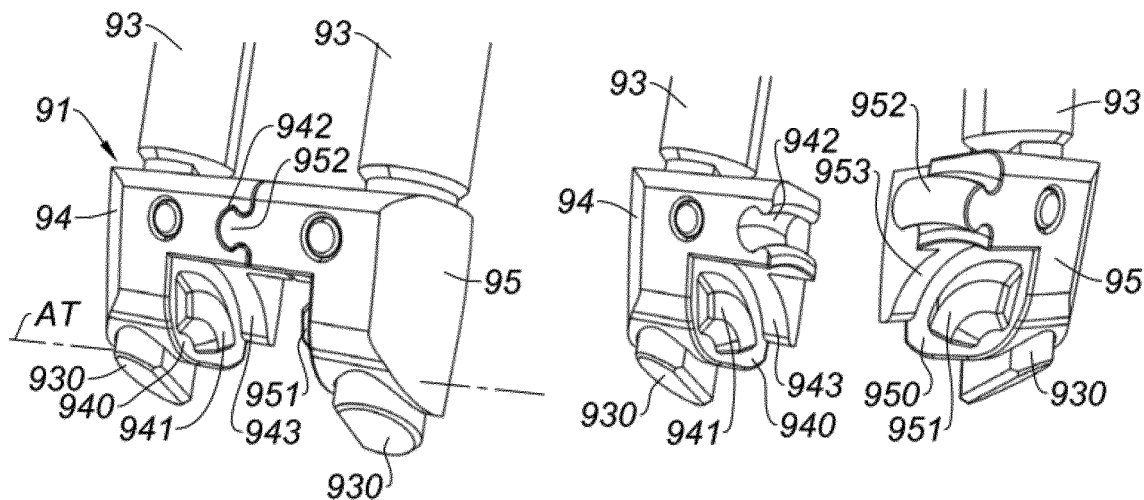
[Fig. 22]
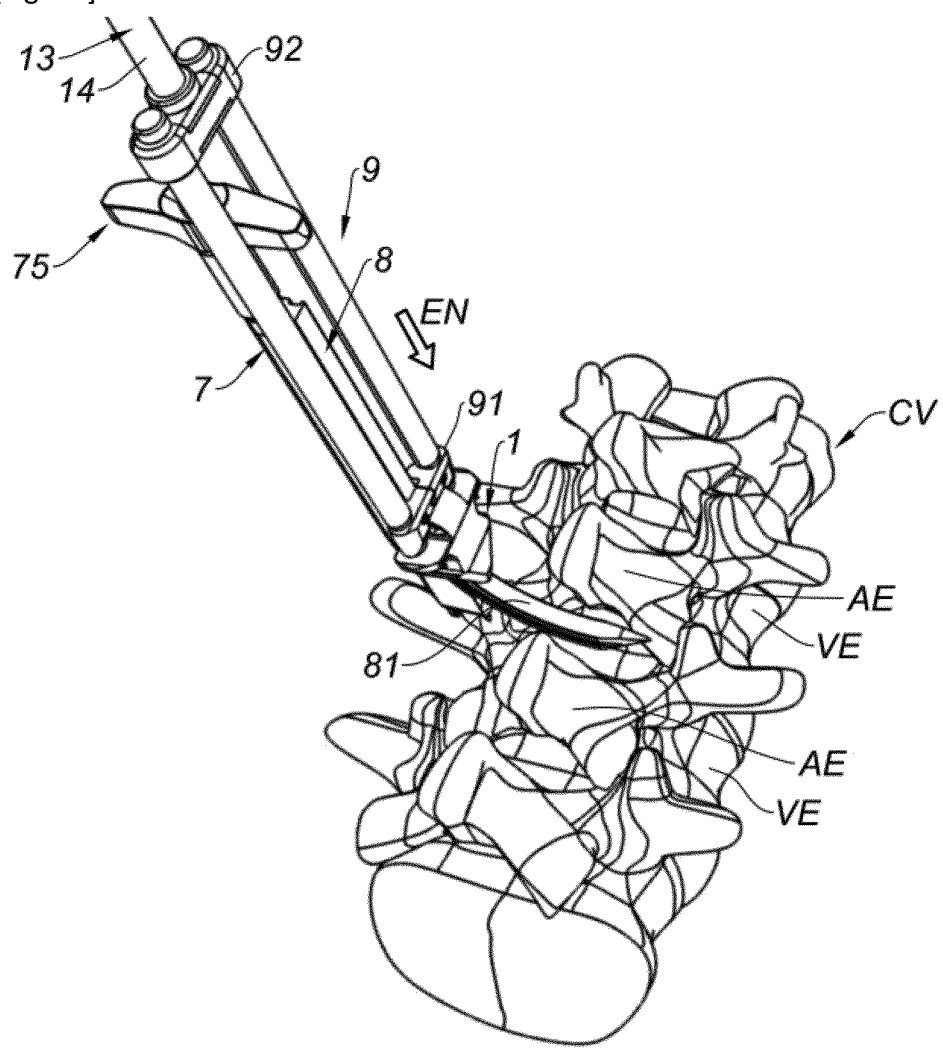

[Fig. 23]
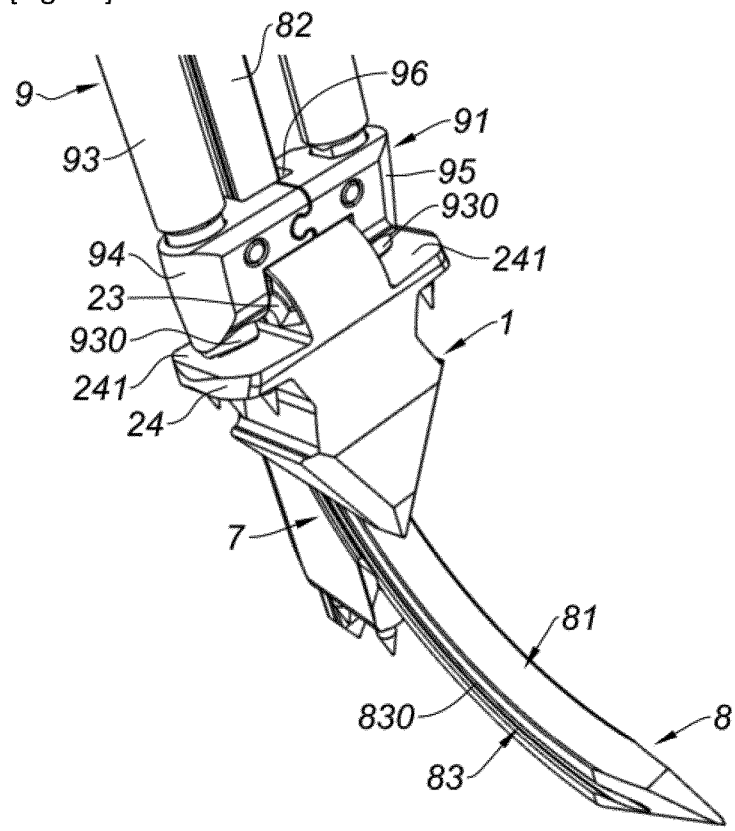
[Fig. 24]
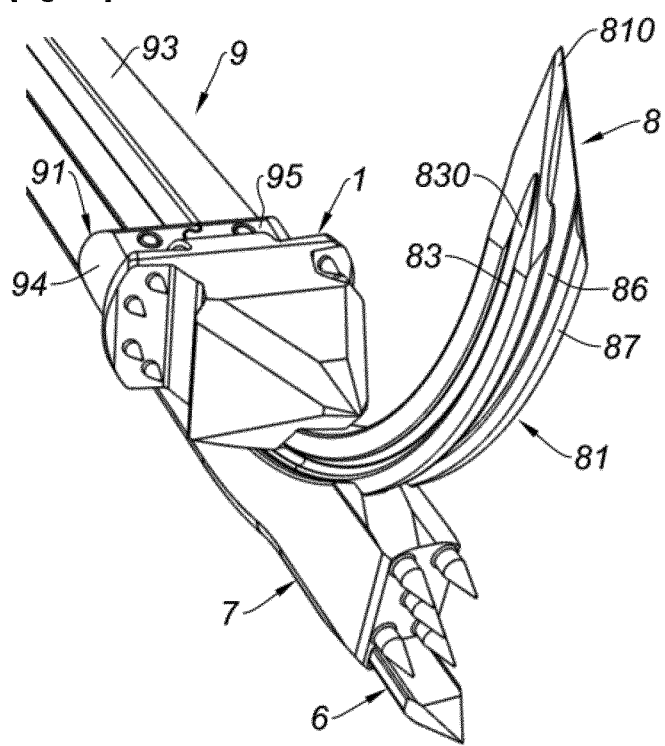

[Fig. 25]
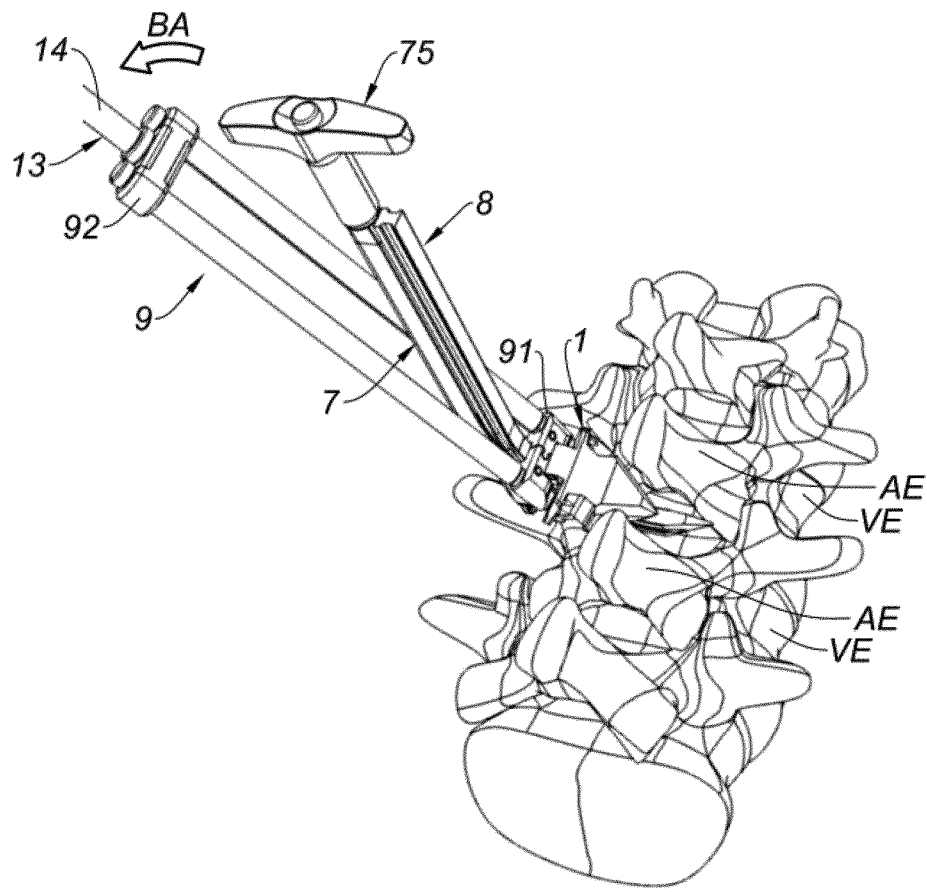
[Fig. 26]
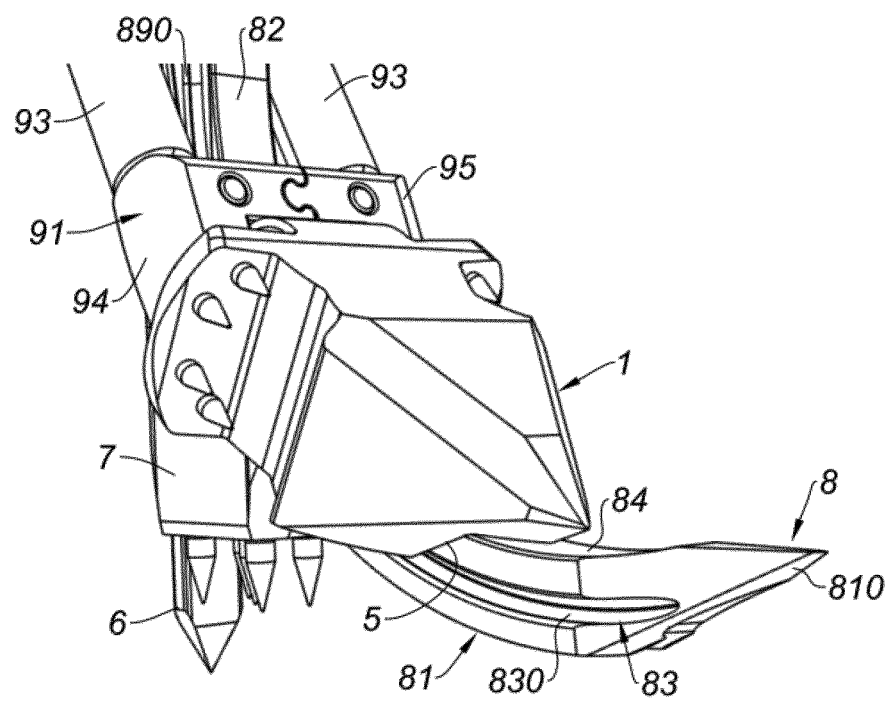

[Fig. 27]
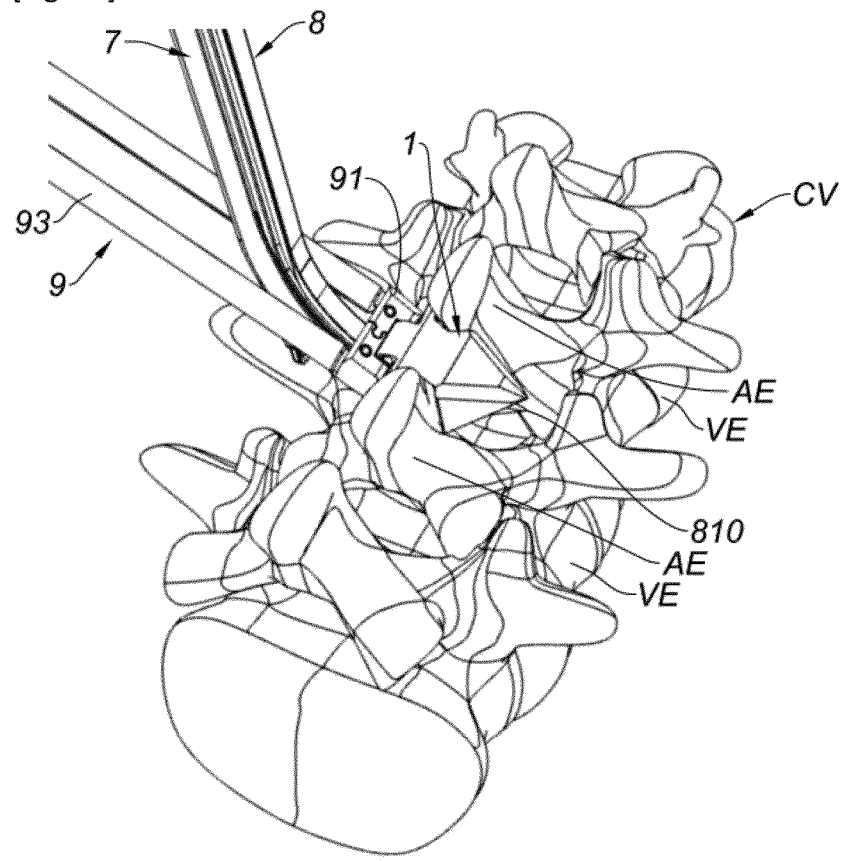
[Fig. 28]
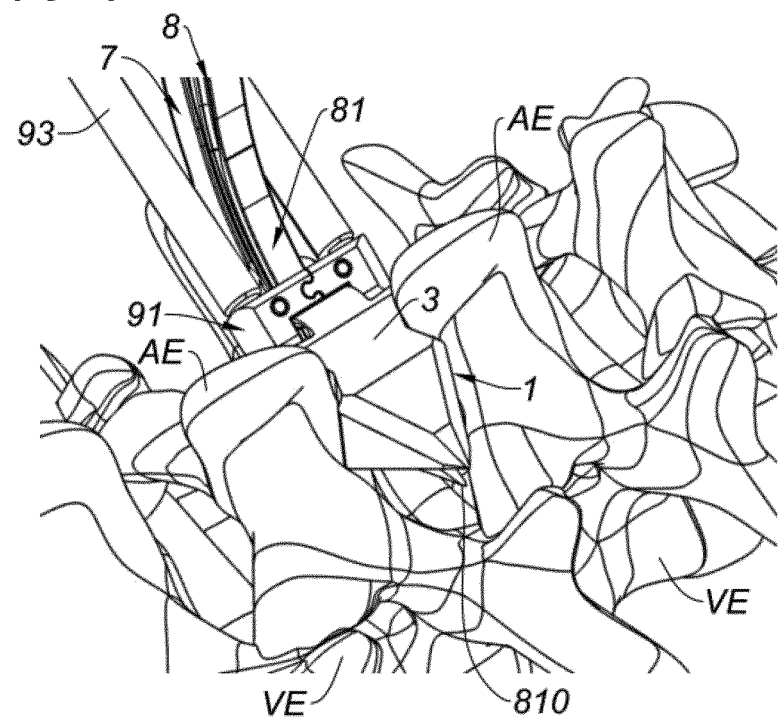

[Fig. 29]
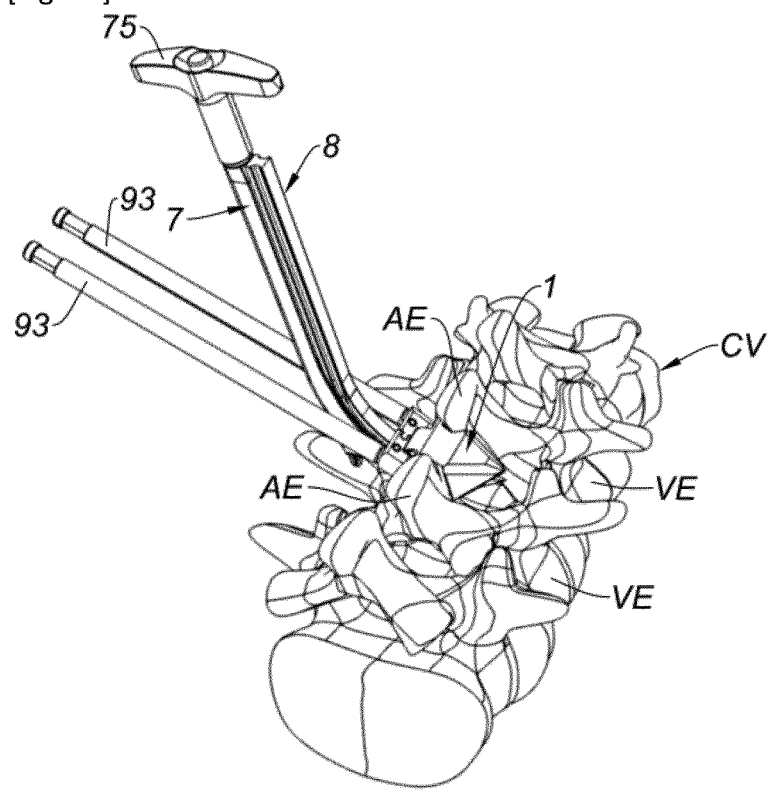
[Fig. 30]
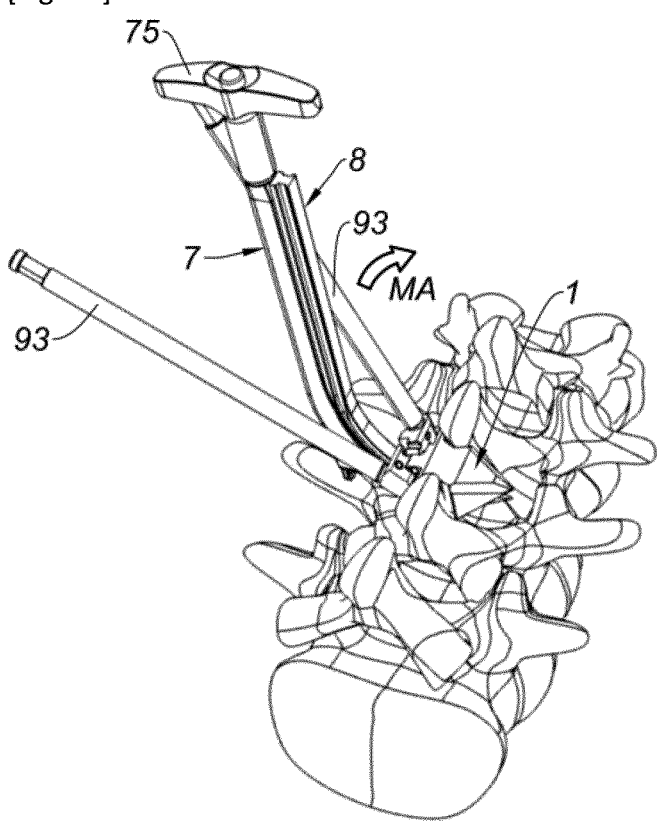

[Fig. 31]
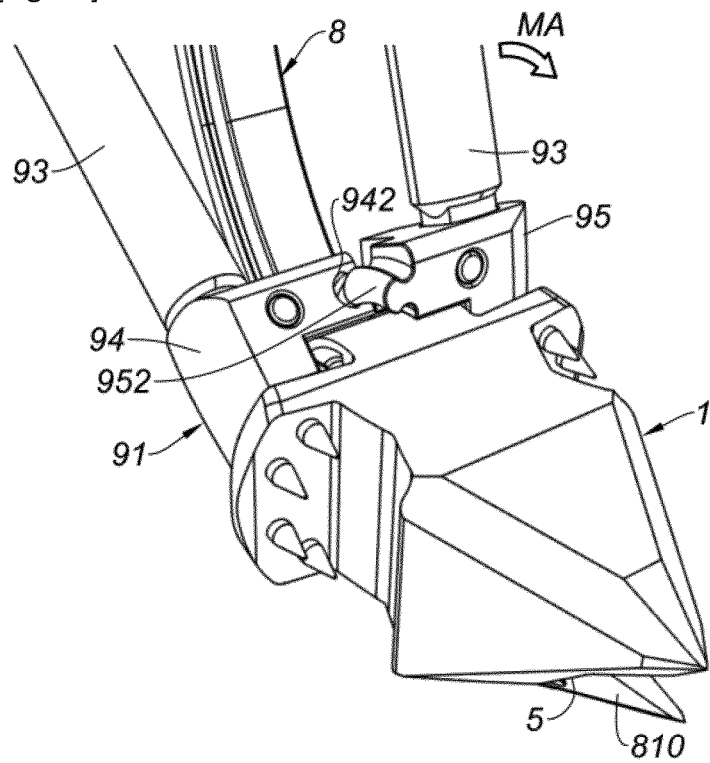
[Fig. 32]
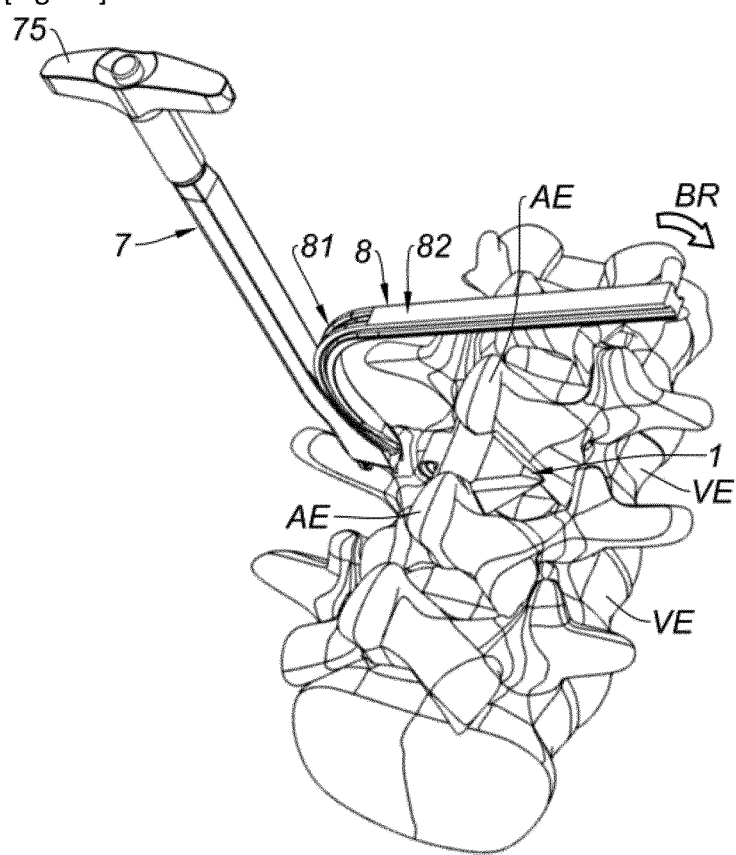

INTERSPINOUS IMPLANT AND ASSOCIATED IMPLANTATION ANCILLARY

TECHNICAL FIELD

The disclosure relates to the technical field of interspinous vertebral implants, and also ancillaries for implanting such interspinous vertebral implants.

BACKGROUND

Interspinous vertebral implants are implants intended to be located between the spinous processes of two adjacent vertebrae. Such implants enable the distraction of two adjacent spinous processes relative to one another, that is to say the obtainment of a gap or a spacing therebetween.

In particular, the disclosure finds its application in the treatment of lumbar pains for example.

An interspinous vertebral implant known from the state of the art, in particular from the document US 2012/0265246, includes an implant body comprising a central portion, intended to extend between two adjacent spinous processes, a front portion, having a profiled shape adapted to move the spinous processes away from the vertebrae progressively and clear a way up to between the two vertebrae and a guide channel in the form of a rectilinear guide hole formed through the implant body, opening only onto the front and rear ends of the implant body, and intended to receive a guide needle.

A surgical intervention is necessary to implant the implant between two vertebrae. This intervention may be percutaneous or open and is carried out via a lateral approach of the patient in the context of the document US 2012/0265246, although a dorsal approach could also be considered but with other models of interspinous vertebral implants. In any case, such an intervention requires significant equipment to locate the accurate location of the implantation and to clear a way up to said location.

Indeed, according to the document US 2012/0265246, a guide needle is used in particular intended to fit into the rectilinear guide hole formed in the implant to guide it during the implantation thereof, and along which two kinds of tools allow clearing the tissues blocking access to the intervertebral space and move the spinous processes partially or temporarily away for a better implantation. The first tool has a head with a screw-like shape or with a smooth profiled shape and slips along the guide needle. The first tool is configured to move the spinous processes temporarily away while sectioning the interspinous ligament.

Once this first clearance is completed, a second tool is inserted along the guide needle, the second tool has the same overall shape as the first tool but has a larger dimension, so as to clear more tissues and to prepare more largely the location of the implantation. It is described that several tools could be used successively, until the location is completely cleared or has a dimension that is large enough to receive the implant. The implant is then placed in the cleared location by slipping along the guide needle.

This known and described method is constraining, because it requires several operations in order to place the implant, it requires a large number of tools before implantation. Furthermore, the surgery by lateral approach is often practiced under general anesthesia which implies a long, complex procedure, with a wide opening in the patient. Moreover, the risk of an improper position is considerable because of the distance between the skin and the insertion area.

The state of the art could also be illustrated by the teachings of the document U.S. Pat. No. 8,672,977 which discloses an interspinous vertebral implant including an articulated-type implant body, provided with a plurality of successive and interconnected segments, so as to be at first in a linear configuration (for the insertion thereof) and then in a curved configuration (once implanted between two adjacent spinous processes). Thus, at rest, this implant body is in a linear configuration and is crossed by a flexible contraction element which passes through a channel that is in the form of aligned holes formed in the segments. At rest, these holes are aligned and the channel is linear for an introduction of the flexible contraction element, which will be used to pull on a segment at the front of the implant body, in order to be able to make it switch from the linear configuration into the curved configuration.

However, the implant described in this document U.S. Pat. No. 8,672,977 has the drawback of being formed by an articulated body, that switches from the linear configuration into the curved configuration, which confers thereon a mechanical strength that is reduced, and necessarily less reliable, to ensure a distraction of two adjacent spinous processes. Moreover, when switching from the linear configuration into the curved configuration during the implantation thereof, there are risks of jamming of matter between the segments of the implant body which are at first spaced apart and are then in contact, which might cause pinches and damages in the patient, and also hinder the implantation.

It is also known from the document U.S. Pat. No. 9,101,409 to use an interspinous vertebral implant including an axisymmetric shell type implant body, comprising a rear portion, a refined central portion and a streamlined front portion, where an axial hole is formed at the center of the implant so as to cross it over the entire length thereof; this axial hole being intended to make the implant body slide along a rectilinear guide rod via a lateral approach by means of a pusher screwdriver that as a hexagonal head fitted into a hexagonal orifice provided at the rear of the axial hole, so that the implant is set in place through a movement combining a lateral push and a rotation, which is equivalent to an implantation by <<screwing>>. It should be noted that the implant body also has grooves formed along the longitudinal direction over half the front portion, the entirety of the central portion and half the rear portion; such grooves being very thin and intended to confer flexibility on the implant, in order to enable it to be contracted during implantation thereof and thus reduce stress on the patient.

As mentioned before, by its implantation via a lateral approach, the implant of the document U.S. Pat. No. 9,101,409 has drawbacks with regards to the complexity of the implantation procedure, performed essentially in a blind and therefore in a non-reliable manner, and also with regards to the trauma for the patient, despite the grooves that could be insufficient to reduce such a stress. Moreover, its implantation by <<screwing>> induces torsions on the tissues and on the spinous processes, which could be sources of traumatisms.

It is also known from the document US2012/0226313 to use an interspinous vertebral implant including an arcuate-shaped implant body, provided with a lateral slot intended to receive two blocking plategers, and provided with a screw at the rear adapted to apply a clamping force on one of the two blocking plategers; the two blocking plategers being intended to make the two adjacent spinous processes depart to the right and to the left, whereas the implant body is housed between these two spinous processes. Nevertheless, such an implant has a limited mechanical reliability with an implant composed by three elements (an implant body and two blocking plategers) that shall be assembled together. This implant cooperates with an implantation ancillary comprising a platform centered on a punch and which serves as a support to the other elements, with a major drawback in connection with the instability of such a platform throughout all operation, not to mention its traumatic appearance as it involves several incisions, one to pass the implant body and one to two others to as the two blocking screws. The other elements consist of a curved rod with a 90 degrees arcuate shape which is secured to a lever arm pivotably articulated on the platform, and a curved guide tube which defines a curved channel and which is secured to a lever arm pivotably mounted on the platform. During the implantation, once the platform is in place, and despite its lack of stability, the curved rod pivots on the platform so as to position its tip between the two spinous processes, and then the curved guide tube also pivots on the platform while being guided by the curved rod which lies in the curved channel. Afterwards, the curved rod is removed, and it is then possible to push the implant body inside the curved channel of the curved guide tube, until positioning between the two spinous processes. Finally, the two guide fingers will slide into two other curved tubes also pivotably mounted on the platform. The implantation method described in this document US2012/0226313 has several drawbacks, including the aforementioned lack of stability of the platform, as well as the traumatic insertions of the curved rod and of the three curved tubes because of their 90 degrees curbed shapes which confer thereon dimensions such that their implantations are necessarily traumatic because their insertions involve long displacements.

SUMMARY

The disclosure aims, among other, at getting rid of an articulated implant body, by retaining the use of a non-articulated implant body that is more reliable and less traumatic during the implantation thereof.

The disclosure aims at overcoming all or part of the aforementioned drawbacks by providing an interspinous vertebral implant suited for a simpler method of implementation via a primarily dorsal and marginally lateral approach, that is to say which involves an approach that is dorsal yet slightly eccentric with respect to the dorsal axis (or axis of the vertebral column). Indeed, the opening on the patient is performed on the back on a portion that is as minimum as necessary determined according to the insertion area of the implant and according to the size of the implant and the size of the implantation tool, which allows for a reliable and accurate implantation of the implant under local anesthesia, and therefore without a heavy surgical intervention with a general anesthesia, thereby minimizing the risks of postoperative complications.

The disclosure also proposes an implantation ancillary that is specially adapted for an interspinous vertebral implant according to the disclosure, and which is adapted for a method for implantation between the spinous processes of two adjacent vertebrae (and not between the vertebral endplates) that is simpler via a primarily dorsal approach.

To this end, the disclosure provides an interspinous vertebral implant including an implant body extending along a longitudinal axis and comprising successively along said longitudinal axis:
 a rear portion having a rear end,
 a central portion shaped so as to extend between two spinous processes of two adjacent vertebrae, said central portion extending the rear portion, and
 a front portion extending the central portion, opposite to the rear portion, while tapering up to a streamline-shaped front end,
wherein said implant body has:
 an anterior face intended to be directed towards the vertebrae,
 a guide channel formed in the implant body from its rear end up to its front end, said guide channel being shaped so as to receive at least one portion of an implantation spindle of an implantation ancillary;
 said interspinous vertebral implant being remarkable in that the guide channel extends from the rear end up to the front end along a curvilinear direction, said guide channel being formed in the anterior face so that said guide channel forms an anterior groove of curvilinear shape and opening outside into said anterior face of the implant body.

Thus, thanks to such an anterior groove, such an implant according to the disclosure allows receiving an implantation spindle which is curved in a predetermined manner. Consequently, such an implant according to the disclosure enables an intervention using a primarily dorsal approach, which is difficult, and even impossible, to conceive with a rectilinear guide hole of the state of the art. Indeed, its curvilinear shape enables an intuitive and progressive insertion between the vertebrae by resorting to a dorsal opening, slightly eccentric with respect to the dorsal axis, thereby promoting a direct implantation in the determined implantation area.

In the present disclosure, the following terms are defined:
 by <<front>>, it should be understood the portion of the implant body that is intended to penetrate at first in the body of the patient;
 by <<rear>>, it should be understood the portion of the implant body that is intended to penetrate at least in the body of the patient;
 by <<streamlined shape>>, it should be understood the shape of the front end which thins along the longitudinal direction from the rear to the front;
 by <<curvilinear direction>>, it should be understood that the direction of the through channel follows a curve, and nota line, and for example a curve in a circular arc over a given radius of curvature;
 by <<anterior face>>, reference is made to the anatomy of the patient to indicate a face directed towards the vertebrae;
 by <<posterior face>>, reference is made to the anatomy of the patient to indicate a face directed opposite to the vertebrae, on the side of the skin of the back;
 by <<lower face>>, reference is made to the anatomy of the patient to indicate a face directed towards a spinous process of the underlying vertebra (the bottom vertebra);
 by <<upper face>>, reference is made to the anatomy of the patient to indicate a face directed towards a spinous process of the above vertebra (the top vertebra).

The implant according to the disclosure may include one or more of the following features considered alone or in combination.

According to one feature, the anterior groove is formed continuously (in other words without any interruption or break-up) in the anterior face of the implant body from the rear end up to the front end, so as to continuously open into the anterior face.

According to another feature, the implant body is not articulated, so that, in a rest position (before implantation) as well as in an implanted position (once implanted between the two spinous processes), the anterior groove is curvilinear shaped along the same curvature.

According to another feature, the anterior groove has a convex shape having a given radius of curvature, with a center of curvature located facing a posterior face of the implant body, opposite to the anterior face.

The convex shape, which corresponds to a curvilinear direction in a circular arc, is advantageous as it enables the implant to switch from a vertical orientation into a horizontal orientation along a flexible and seamless guide path of the implant throughout the insertion thereof.

According to one possibility, the anterior face has a convex shape having the radius of curvature.

Thus, the guidance of the implant may also be done by following this anterior face which is also curvilinear.

According to another possibility, the anterior groove is internally delimited by a bottom wall offset in depth with respect to the anterior face, said bottom wall having a convex shape having a given radius of curvature.

Thus, the guidance of the implant may also be done by following this bottom wall which is also curvilinear.

According to one variant, the bottom wall and the anterior face have the same center of curvature, and the radius of curvature of the bottom wall is smaller than the radius of curvature of the anterior face.

According to another possibility, the anterior groove is externally delimited by retaining lips with a convex shape having the radius of curvature, said retaining lips being disposed facing the bottom wall and extending facing each other so as to delimit a narrow space in comparison with the interior of the anterior groove.

Thus, the anterior groove has a <<C>>-like section, with retaining lips at the terminations of the <<C>> which will ensure a function of retaining the implant, in other words of holding the implant on the implantation spindle without any risk of getting out of the implantation spindle during the insertion.

In a particular embodiment, the radius of curvature is comprised between 20 and 300 millimeters.

An advantage provided by such radii of curvature is to facilitate the surgical intervention using a primarily dorsal approach (with a dorsal opening slightly eccentric with respect to the dorsal axis), and to limit the size of the incision.

In a particular embodiment, the rear portion has pivot means around a transverse axis extending transversely with respect to the longitudinal axis to enable a pivoting of said implant body relative to complementary pivot means provided on an implant-holder of the implantation ancillary.

Thus, these pivot means will enable the implant to easily pivot during the insertion thereof, its insertion being done along an insertion path having at least one curvilinear component, which will facilitate this insertion because the implant will be coupled and held by this implant-holder along the entirety of this curvilinear component of the path.

According to one feature, the rear portion has two opposite lateral faces, respectively an upper face and a lower face, and the pivot means are provided on said opposite lateral faces in the form of recesses or of protrusions shaped at least partially in a circular arc centered on the transverse axis.

Thus, the pivot means operate by form-fitting, complementary pivot means provided on the implant-holder having complementary shapes for a coupling by form-fitting that enables a relative pivoting between the implant and the implant-holder.

In a particular embodiment, the front portion comprises facets directly connected to each other by sharp edges converging towards the front end tapering into a tip.

The advantage provided by the sharp edges is to allow perforating and slicing the interspinous ligament easily and clearing a way for the implant.

According to one variant, the tip and the facets of the front portion define a frustoconical, pyramidal or trapezoidal shaped volume. An advantage provided by such a shape is to facilitate the perforation of the ligament areas while remaining compact.

In a variant of the disclosure, the sharp edges can be obtained by a profile using a simple machining.

In a variant of the disclosure, at least one of the sharp edges and preferably all sharp edges are rectilinear, which enables a neat perforation of the ligament areas.

In an advantageous embodiment, the rear portion comprises, at an interface with the central portion, at least one blocking plate projecting on a lower side of the rear portion or on an upper side of the rear portion, opposite to the lower side.

Also, the or each blocking plate extends at the front of the rear portion, and therefore at the rear of the central portion, between the rear portion and the central portion, and it forms a plate adapted to abut against a spinous process, so as to stop the implant in its insertion path and ensure an accurate positioning between the two spinous processes. Thus, during the implantation of the implant, the or each blocking plate prevents the displacement of the implant out of the interspinous space by being pressed each against an adjacent spinous process, in order to avoid an unintentional removal of the implant.

Advantageously, the rear portion comprises, at the interface with the central portion, a blocking plate projecting on the lower side of the rear portion and another blocking plate projecting on the upper side of the rear portion.

According to one variant, the two blocking plates are coplanar.

According to another variant, the two blocking plates are identical and symmetrical with respect to a midplane containing the longitudinal axis.

According to one possibility, the at least one blocking plate extends from the concerned side of the rear portion in a plane orthogonal to the longitudinal axis or inclined with respect to the longitudinal axis by an angle comprised between 60 and 120 degrees.

Thus, when the or each blocking plate extends from the rear portion in a plane substantially perpendicular to the longitudinal axis of the implant body, it is naturally anchored on the corresponding spinous process.

According to another possibility, the at least one blocking plate is fixed or articulated on the rear portion.

The advantage of a fixed blocking plate is to have an implant body with an easy and inexpensive design.

In the case where the blocking plate is articulated, the latter is then movable between at least one deployed position in which it extends along an axis substantially perpendicular to the longitudinal axis of the implant body and a stowed position in which it extends, preferably against the considered side of the rear portion, along an axis substantially parallel to the longitudinal axis of the implant body.

According to another possibility, the at least one blocking plate has a front face directed in the direction of the front end and on which is provided at least one anchoring relief configured to enable anchorage on a spinous process, such as an anchoring relief in the form of a spike.

This front face is intended to lie facing one of the spinous processes, and the anchoring relief(s) will confer a stable anchorage in this spinous process in the final position of the implant.

According to one variant, the at least one blocking plate has several anchoring reliefs.

According to another variant, the at least one spike extends along an axis substantially parallel to the longitudinal axis of the implant.

According to another variant, the front face of the at least one blocking plate is coated with an osteointegration material, promoting the adhesion between the bone and the implant body, such as for example a porous material.

In a particular embodiment, the central portion has two opposite lateral faces, respectively an upper face and a lower face, which are concave so as to define two recessed lateral faces adapted to fit between the two spinous processes.

It should be noted that the upper face of the central portion is intended to bear on the spinous process of the underlying vertebra, whereas the lower face of the central portion is intended to bear on the spinous process of the underlying vertebra. Thus, this recessed shape of these two faces allows conforming to the base of the two spinous processes and also promotes a slight elastic deformation adapted to ensure a soft distraction between the adjacent spinous processes, relative to one another and thus reducing the lordosis at this level.

According to one variant, the implant body is made of at least one biocompatible sterilizable material. As non-limiting examples, the implant body may be made of a material selected amongst titanium, a titanium-based alloy, a steel, a biocompatible plastic material such as PolyEtherEtherKetone (PEEK), poly(methyl methacrylate) (PMMA), etc.

The disclosure also relates to an implantation ancillary, intended for guidance and positioning of an interspinous vertebral implant according to the disclosure between two spinous processes of two adjacent vertebrae, this implantation ancillary comprising:

an implant-holder having a distal portion and a proximal portion opposite to each other, said distal portion being provided with support means shaped so as to support said interspinous vertebral implant;

an implantation spindle having a distal end portion which extends up to a free and tip-shaped distal end, said distal end portion having a curved shape and on which is provided a curved guide rail with a shape complementary with an anterior groove of the interspinous vertebral implant to enable a sliding guidance of said interspinous vertebral implant along a posterior face of said distal end portion by fitting of the guide rail inside the anterior groove, said guide rail extending up to the free distal end.

Thus, the interspinous vertebral implant will be able to be guided by the guide rail of this curved implantation spindle, along a path that is at least partially curvilinear which enables an intuitive and progressive insertion between the two spinous processes of the vertebrae. In other words, with its anterior groove, the implant will be able to position itself and slide on the curved implantation spindle to enable an intervention using a primarily dorsal approach, along a curvilinear path (enabled thanks to the shape of the curved implantation spindle) and by resorting to a dorsal opening, slightly eccentric with respect to the dorsal axis, thereby promoting a direct implantation in the determined implantation area.

In other words, thanks to such an implantation ancillary according to the disclosure, the implantation spindle is directed in a curved manner on its distal end portion, which enables a surgical intervention using a primarily dorsal approach. Furthermore, thanks to its anterior position with respect to the implant, the implantation spindle is brought to protect the nervous elements present in the vertebral channel.

It should be noted that, in the context of the disclosure, the implantation spindle forms a slender, in particular a curve-shaped, body terminating in a free and tip-shaped distal end, so as to be able to penetrate, by clearing a way through the tissues, into the body of the patient up to an adequate position facing the interspinous space, between the two spinous processes, which is a conventional function of a spindle in the surgical field. Moreover, this implantation spindle has the previously-described particularity, namely the presence of a guide rail on which the interspinous vertebral implant is slidably guided; this sliding being necessarily performed on the implantation spindle (in other words the implant is outside the implantation spindle), and not inside the implantation spindle, because in the surgical field, it is common practice that a spindle does not form a channel or a tube inside which an implant could slip.

It should be also noted that the guide rail provided on the implantation spindle has the function of guiding the interspinous vertebral implant along a curved implantation path, but it has also necessarily the function of preventing or limiting a lateral displacement of the implant in order to avoid that it comes out of the guide rail.

Advantageously, the positioning of the curved distal end portion of the implantation spindle will be done the most anterior as possible at the level of the interspinous space because the optimum situation of the implant at the end of the intervention corresponds to the anterior portion of the interspinous space, an area where the bone is the widest and the most solid. Thus, the curvilinear direction of the guide groove is selected so that the implantation spindle has a satisfactory attack angle to access the interspinous space.

In the present disclosure, the term <<proximal>> refers to a portion or to an end that is the closest to the hand of the surgeon during the implantation of the implant, and the term <<distal>> refers to a portion or to an end that is the farthest from the hand of the surgeon during the implantation, or in other words the closest to the patient at the time of intervention.

According to one feature, the implantation spindle is solid, and it does not form a tube or a channel.

According to one possibility, the distal end portion of the implantation spindle is curved in a circular arc over an angular sector comprised between 60 and 120 degrees.

In a particular embodiment, the distal end portion of the implantation spindle is curved in a circular arc over a radius of curvature comprised between 20 and 300 millimeters.

An advantage provided by such radii of curvature is to facilitate the surgical intervention using a primarily dorsal approach, and limit the size of the incision.

According to another possibility, the implantation spindle comprises a proximal end portion which extends the distal end portion up to a free proximal end, and the guide rail is prolonged, from the distal end portion, by a longitudinal rail formed on the proximal end portion up to the proximal end.

Thus, the interspinous vertebral implant can be slip on the longitudinal rail at the level of the proximal end, so as to slide in the direction of the curved distal end portion in order to pass into the curved guide rail to slide and follow a curvilinear path.

It is obvious that, in the context of the disclosure, the guide rail and the longitudinal rail could form one continuous rail on which the interspinous vertebral implant could fit from the proximal end up to the distal end.

In other words, the guide rail and the longitudinal rail are provided together on the implantation spindle with the function of guiding the interspinous vertebral implant along a complete implantation path that is rectilinear and then curved, but this guide rail and this longitudinal rail also necessarily have the function of preventing or limiting a lateral displacement of the implant in order to avoid that it comes out of the guide rail and of the longitudinal rail.

According to one possibility, at least one amongst the proximal end portion and the longitudinal rail is rectilinear, in other words this proximal end portion is rectilinear and/or this longitudinal rail is rectilinear.

Thus, the interspinous vertebral implant will follow an insertion path having at first a linear component (slip on the longitudinal rail) and then finally a curvilinear component (slip on the curved guide rail), which enables the implant to switch from a vertical orientation (outside the patient) into a horizontal orientation (inside the patient in the interspinous space).

According to one feature, the guide rail is formed on at least one outer face of the distal end portion of the implantation spindle.

In other words, the guide rail is formed outside the implantation spindle, for a sliding of the implant on the implantation spindle (and not inside a tube or a channel).

According to another feature, the free and tip-shaped distal end of the implantation spindle has a tip angle smaller than or equal to 90 degrees, and preferably smaller than or equal to 60 degrees, and possibly smaller than or equal to 45 degrees.

Indeed, a small tip angle promotes the penetration of the implantation spindle through the tissues.

In a particular embodiment, the distal end portion of the implantation spindle has two opposite lateral faces, respectively an upper face and a lower face, and the guide rail is formed in the form of two notches formed in said respective lateral faces.

Such notches are adapted to receive respectively the previously-described retaining lips and thus allow for a stable and reliable guidance over the entire distance.

According to one feature, the distal end portion of the implantation spindle has an anterior face, opposite to the posterior face along which the implant slides, and on which is provided a first pivot guide means, and the implantation ancillary comprises a primary support having a distal portion on which are provided at least one anchoring relief for anchorage, and a second pivot guide means adapted to cooperate with the first pivot guide means to pivotably guide said implantation spindle during an insertion of its distal end portion between the two spinous processes.

Thus, this primary support will be anchored in a vertebra, in an area located in a midplane passing between the two spinous processes, and afterwards this primary support will be used to direct the implantation spindle to fit its distal end portion between the two spinous processes, using a pivoting or tilting movement of the implantation spindle.

In a particular embodiment, the first pivot guide means and the second pivot guide means respectively comprise an arcuate rail and an arcuate slide with complementary shapes.

According to one variant, the first pivot guide means and the second pivot guide means are shaped so as to pivotably guide the implantation spindle along a pivot angle comprised between 60 and 120 degrees, and in particular in the range of 90 degrees.

According to another feature, the primary support has a proximal portion coupled to a holding grip provided with a gripping head.

A main function of such a holding grip is to enable a gripping by the surgeon and therefore to allow to the surgeon a set-up and a holding of the primary support in order to anchor it in the vertebra, in particular by exerting a pushing force, and where necessary an impaction force on the gripping head, preferably repeatedly, to ram the primary support.

According to one variant, the holding grip is distinct from the primary support and is secured to the primary support or the holding grip and the primary support are integrally made in one-piece.

According to another feature, the primary support has a distal hole opening into a distal face of the distal portion of the primary support, and the implantation ancillary comprises a positioning punch provided with a tip-shaped distal end intended for anchorage in a vertebra, said positioning punch being shaped so as to slidably guide the primary support longitudinally by insertion of the positioning punch inside the distal hole.

Thus, this positioning punch will be anchored in a vertebra, at an accurate point determined by the surgeon and located substantially in the midplane passing between the two spinous processes, and it will be used to guide the primary support to position it in the desired area.

In a particular embodiment, the support means provided on the distal portion of the implant-holder comprise complementary pivot means shaped so as to cooperate with the pivot means of the rear portion of the interspinous vertebral implant in order to enable a pivoting of this vertebral implant around a transverse axis.

According to one possibility, the support means comprise two support elements having inner faces facing each and respectively provided with recesses or protrusions shaped at least partially in a circular arc centered on the transverse axis and forming the complementary pivot means.

Thus, the interspinous vertebral implant is wedged between the inner faces of the two respective support elements, while being pivotably movable between these two inner faces.

Furthermore, the pivot means operate by form-fitting, the complementary pivot means provided on the implant-holder having complementary shapes for coupling by form-fitting which enables a relative pivoting between the implant and the implant-holder.

According to another possibility, the two support elements are detachably attached to one another and, to this end, are provided with removable attachment means so that the two support elements can be configured between an attached configuration to allow supporting the interspinous vertebral implant, and a detached configuration to allow releasing the interspinous vertebral implant from the implant-holder.

In this manner, once the interspinous vertebral implant is in place between the two spinous processes, all it needs is to detach the two support elements from each other to allow releasing the interspinous vertebral implant and thus removing the implant-holder while leaving the interspinous vertebral implant in place.

According to one possibility, the removable attachment means are formed by an upper slide and by an upper rail which are provided on the respective support elements.

According to another possibility, the upper slide and the upper rail are both arcuate and with complementary shapes and extend between an anterior face and a posterior face of the distal portion of the implant-holder, to form pivot guide means adapted to cooperate together so as to pivotably guide a support element relative to the other support element around the transverse axis.

Thus, the detachment between the two support elements is done by pivoting, without hindering the implant.

According to another possibility, the distal portion and the proximal portion of the implant-holder are linked by two rods, said rods having distal ends fastened on the respective support elements and proximal ends, opposite to their distal ends, which are removably fastened on the proximal portion.

Advantageously, the distal ends of the rods have respective terminations which project from the respective support elements, in order to be able to bear against respective blocking plates of the implant.

In a particular embodiment, the implantation ancillary comprises an impactor removably mounted on the proximal portion of the implant-holder.

According to one feature, the impactor comprises an impaction rod provided with a distal end fastened on the proximal portion of the implant-holder, and with a proximal end, opposite to the distal end, and on which a grip is fastened.

According to another feature, the impactor further comprises an impaction sleeve slidably mounted around the impaction rod, between the grip and the proximal portion of the implant-holder.

BRIEF DESCRIPTION OF THE DRAWINGS

Other features and advantages of the present disclosure will appear upon reading the detailed description hereinafter, of a non-limiting example of implementation, made with reference to the appended schematic figures wherein:

FIG. 1 is a perspective illustration on the posterior side of an example of an interspinous vertebral implant according to the disclosure;

FIG. 2 is a front illustration (front side) of the implant of FIG. 1;

FIG. 3 is a bottom illustration (internal face side) of the implant of FIG. 1;

FIG. 4 is a perspective illustration on the anterior side of the implant of FIG. 1;

FIG. 5 is a back illustration (rear side) of the implant of FIG. 1;

FIG. 6 is an illustration of the posterior side of the implant of FIG. 1;

FIG. 7 is an illustration of the anterior side of the implant of the FIG. 1;

FIG. 8 is a perspective illustration (view of the back and of the posterior side) of the implant of FIG. 1 in place between two spinous processes;

FIG. 9 is a perspective illustration (view of the front and of the posterior side) of the implant of FIG. 1 in place between two spinous processes;

FIG. 10 is an illustration of the posterior side of the implant of FIG. 1 in place between two spinous processes; and FIG. 11 is an illustration of a first step of inserting a positioning punch of the implantation ancillary according to the disclosure;

FIG. 12 is an illustration of a second step of inserting a primary support of the implantation ancillary according to the disclosure;

FIG. 13 is a perspective illustration of the distal portion of the primary support of FIG. 12, according to two distinct viewpoints;

FIG. 14 is an illustration of a third step of coupling a holding grip on the primary support, and of a fourth step of inserting an implantation spindle of the implantation ancillary according to the disclosure;

FIG. 15 is a perspective illustration of the holding grip of FIG. 14 alone;

FIG. 16 is an enlarged and perspective illustration of the distal portion of the primary support on which the distal end portion of the implantation spindle is guided during the fourth step of FIG. 14;

FIG. 17 is a perspective illustration of the implantation spindle of FIG. 14 alone, according to several viewpoints and entirely (the left-side view) or partially (the three right-side views);

FIG. 18 is an illustration of a fifth step of pivoting (or tilting) the implantation spindle relative to the static primary support;

FIG. 19 is a perspective illustration of the implantation ancillary set according to the disclosure, comprising an ancillary-holder supporting the implant of FIG. 1, and further comprising an impactor mounted on the implant-holder;

FIG. 20 is a perspective illustration of the implant-holder of FIG. 19 alone;

FIG. 21 is a perspective illustration of the distal portion of the implant-holder of FIG. 19, with its two support elements in the attached configuration (to the left) and in the detached configuration (to the right);

FIG. 22 is an illustration of a sixth step of inserting the ancillary-holder and impactor set of FIG. 19, the ancillary-holder supporting the implant of FIG. 1;

FIG. 23 is an enlarged and perspective illustration of the distal portion of the primary support and of the distal end portion of the implantation spindle on which slides the implant carried by the implant-holder of FIG. 19;

FIG. 24 is an enlarged and perspective illustration of the distal portion of the primary support and of the distal end portion of the implantation spindle on which slides the implant carried by the implant-holder of FIG. 19;

FIG. 25 is an illustration of the beginning of a seventh step of pushing the implant of FIG. 1 which slides on the implantation spindle in the direction of the interspinous space between the two spinous processes;

FIG. 26 is an enlarged and perspective illustration of the implant which slides on the implantation spindle at the beginning of the seventh step of FIG. 25;

FIG. 27 is an illustration of the end of the seventh step of pushing the implant of FIG. 1 which has slid on the implantation spindle and which is henceforth positioned between the two spinous processes;

FIG. 28 is an enlarged and perspective illustration of the implant on the implantation spindle at the end of the seventh step of FIG. 27;

FIG. 29 is an illustration of an eighth step of removing the impactor off the implant-holder;

FIG. 30 is an illustration of a ninth step of unlocking the implant-holder by making its two support ends switch into the detached configuration;

FIG. 31 is an enlarged and perspective illustration of the implant and of the implant-holder during the ninth step of FIG. 30; and FIG. 32 is an illustration of a tenth step of removing the implantation spindle, after having removed the implant-holder following the ninth step of FIG. 30.

DETAILED DESCRIPTION OF THE DRAWINGS

For simplicity, elements that are identical or ensuring the same function will bear the same references for the different embodiments.

The implant 1 according to the disclosure will now be described with reference to FIGS. 1 to 7. This implant 1 according to the disclosure is an interspinous vertebral implant including an implant body 10 made of at least one biocompatible material. More specifically, this implant 1 is formed integrally and solely by this implant body 10.

This implant body 10 extends along a longitudinal axis AL and it comprises successively along this longitudinal axis AL:
- a rear portion 2 having a rear end 20,
- a central portion 3 shaped so as to extend between two spinous processes AE (as shown in FIGS. 8 to 10) of two adjacent vertebrae VE, this central portion 3 extending the rear portion 2, and
- a front portion 4 extending the central portion 3, opposite to the rear portion 3, while tapering up to a streamline-shaped front end 40.

Thus, the central portion 3 links the rear portion 2 to the front portion 4, and this central portion 3 extends between the rear portion 2 to the front portion 4.

It should be noted that the central portion 3 may have some elasticity, in comparison with the front portion 2, enabling a bending of the central portion 3 throughout its insertion path, in particular throughout the curvilinear component of this insertion path. Once inserted, this flexibility of the implant body 1 allows preserving movability between the two adjacent vertebrae within a given range. This elasticity of the central portion 3, which contributes in having an implant body 10 with two "areas" with different rigidity/flexibility, may be obtained for example by geometric modifications (for example, lattice-type structure) and/or by the use of different materials.

The rear portion 2 has a half-disk like general shape with its rear end 20 which is rounded or rather a semi-cylindrical shape centered on a transverse axis AT that is perpendicular to the longitudinal axis AL.

This rear portion 2 has two opposite lateral faces 21, 22, respectively an upper face 21 and a lower face 22, with a half-disk like general shape, and means for pivoting around the transverse axis AT are provided on these two lateral faces 21, 22. For this purpose, the pivot means are provided in the form of recesses 23 formed on the respective lateral faces 21, 22 and shaped at least partially as a circular arc centered on the transverse axis AT. As shown in FIG. 3, a recess 23 is in the form of a circular arc shaped recess over an angular sector smaller than 180° C., such as for example and without limitation an angular sector comprised between 20 and 175 degrees.

As explained later on, these recesses 23 are intended to cooperate with complementary protrusions 941, 951 provided on an implant-holder 9 to enable a relative pivoting of the implant body 10 on this implant-holder 9 around the transverse axis AT.

At the junction between the rear portion 2 and the central portion 3, the rear portion 2 comprises a blocking plate 24 projecting on the lower side of the rear portion 2 (on the same side as the lower face 22) and another blocking plate 24 projecting on the upper side of the rear portion 2 (on the same side as the upper face 21).

The two blocking plates 24 are symmetrical with respect to a midplane PM including the longitudinal axis AL and orthogonal to the transverse axis AT, and the blocking plate 24 extends perpendicular to the lower face 22 whereas the other blocking plate 24 extends substantially perpendicular to the upper face 21.

These blocking plates 24 are coplanar extending in a plane substantially orthogonal to the longitudinal axis AL, or more generally in a plane inclined with respect to the longitudinal axis AL by an angle comprised between 60 and 120 degrees. In general, the implant body 10 is symmetrical with respect to this midplane PM.

The two blocking plates 24 project outwardly with respect to the respective lateral faces 21, 22, and also with respect to the central portion 3. The two blocking plates 24 are fastened and integral with the implant body 10. In a non-illustrated variant, the blocking plates 24 are articulated on the respective lateral faces 21, 22 or the blocking plates 24 are removably mounted on the lateral faces 21, 22.

Each of the two blocking plates 24 has a front face 240 directed towards the front end 40, and a rear face 241 opposite to the front face 240 and directed towards the rear end 20.

On each of the front faces 240 of the two blocking plates 24, several spikes 25 are provided forming anchoring reliefs configured to enable anchorage on a spinous process AE. These spikes 25 extend along directions parallel to the longitudinal axis AL. In turn, the rear faces 241 of the two blocking plates 24 are smooth.

The central portion 3 has two opposite lateral faces 31, 32 respectively an upper face 31 and a lower face 32, which are concave so as to define two recessed lateral faces 31, 32 adapted to fit between the two spinous processes AE. In other words, the central portion 3 is thinned at its center so as to conform with the shape of the spinous processes AE. The two blocking plates 24 project outwardly with respect to the respective lateral faces 31, 32.

The front portion 4 has a streamlined shape adapted to perforate ligament areas, and for this purpose, it comprises planar facets directly connected to each other by sharp and rectilinear edges converging towards the front end 40 tapering into a tip.

The implant body 10 also has an anterior face 11 intended to be directed towards the vertebrae VE, and a posterior face 12, opposite to the anterior face 11.

The anterior face 11 has a convex shape having a radius of curvature RC comprised between 20 and 300 millimeters, with a center of curvature located facing the posterior face 12 of the implant body 10. In turn, the posterior face 12 has a convex shape at the level of the central portion 3 and a planar facet shape at the level of the front portion 4.

The implant body 10 also has an anterior groove 5 formed in the anterior face 11 and completely crossing the implant body 10 from its rear end 20 up to its front end 40 so as to form, as described later on, a guide channel shaped so as to receive at least one portion of an implantation spindle 8 of an implantation ancillary described hereinafter.

As clearly shown in FIGS. 4 and 7, this anterior groove 5 is formed continuously in the anterior face 11 of the implant body 10 from the rear end 20 up to the front end 40, so as to continuously open into the anterior face 11.

This anterior groove 5 has a convex shape having the radius of curvature RC, and therefore extends from the rear end 20 up to the front end 40 along a circular arc shaped curvilinear direction. This anterior groove 5 extends in the midplane PM and it is symmetrical with respect to the midplane PM Although some flexibility could be considered for the implant body 10, this implant body 10 does not form in any way an articulated body, in other words this implant body 10 is not articulated, to the extent that in a rest position (a position shown in FIGS. 1 to 7) as well as in an implanted position (a position shown in FIGS. 8 to 10 and 27 to 32), the anterior groove 5 has a curvilinear shape having the same curvature.

The anterior groove 5 is internally delimited by a bottom wall 50 offset in depth with respect to the anterior face by a given depth PR constant from the rear end 20 up to the front end 40, as shown in FIG. 5.

This bottom wall 50 has a convex shape with a center of curvature coincident with the center of curvature of the anterior face 11 and having a radius of curvature RP (not illustrated) smaller than the radius of curvature RC of this anterior face 11. The depth PR is measured along a radial direction passing through the center of curvature, so that RC=RP+PR.

This anterior groove 5 is internally delimited by two lateral walls 51, 52 parallel to the midplane PM and circular arc shaped. The spacing between the two lateral walls 51, 52 delimits the width LA of the anterior groove 5.

The anterior groove 5 is externally delimited by retaining lips 53 with a convex shape having the radius of curvature RC at the level of the anterior face 11. These retaining lips 53 project from the respective lateral walls 51, 52, moreover, they are disposed facing the bottom wall 50 and they extend facing each other so as to delimit a space that is narrow in comparison with the interior of the anterior groove 5. In other words, the spacing EC between the two retaining lips 53 is smaller than the width LA of the anterior groove 5. These retaining lips 53 are integral with the anterior face 11 into which the anterior groove 5 opens.

Each of the retaining lips 53 has a lip thickness or height HL, as shown in FIG. 5, measured along a radial direction passing through the center of curvature. Thus, the anterior groove 5 has a groove height HR, also measured along a radial direction passing through the center of curvature, between the retaining lips 53 and the bottom wall 50, which is such that: PR=HR+HL.

Moreover, the prior groove 5 is shaped so that:
considering a first director and a second director parallel to the longitudinal axis AL, wherein the first director passes through the lowermost point of the bottom wall 50 (substantially at midway between the rear end 20 and the front end 40) and the second director passes through the uppermost point of the retaining lips 53 (at the level of the rear end 20 or of the front end 40), then the anterior groove 5 has a non-zero intermediate height HI, which corresponds to a distance measured between the first director and the second director along a direction orthogonal to the longitudinal axis AL and to the transverse axis AT, as shown in FIG. 5; and
considering a third director parallel to the longitudinal axis AL, where the third director passes through the lowermost point of the retaining lips (substantially at midway between the rear end 20 and the front end 40), then the retaining lips 53 have an overall height HG, which corresponds to a distance measured between the second director and the third director along a direction orthogonal to the longitudinal axis AL and to the transverse axis AT, as shown in FIG. 5.

Such a conformation is advantageous to allow making the implant 1 slide on a longitudinal rail 89 (described later on) along a longitudinal (in other words rectilinear) path and then a curved guide rail 83 (described later on) along a curved or arcuate path.

The anterior groove 5 has at its two respective ends a rear mouth 54 open onto the rear end 20, and a front mouth 55 open onto the front end 40.

The following description, made with reference to FIGS. 11 to 32, relates to the implantation ancillary intended for guidance and positioning of the implant 1 between two spinous processes AE of adjacent vertebrae VE, as well as the method for implanting the implant 1 by means of such an implantation ancillary.

This implantation ancillary is in the form of a kit comprising several distinct functional components cooperating together so as to enable an implantation of the implant 1 using a primarily dorsal approach. These different components of the implantation ancillary will be described progressively with their use in the implementation of the implantation method.

Beforehand, and with reference to FIG. 11, the surgeon determines a reference point located in a lateral portion PL of a vertebra VE, at a lateral distance DL with respect to the axis AC of the vertebral column CV (also called dorsal axis), such a lateral distance DL being determined beforehand before the surgery—for example between 5 and 70 millimeters. This reference point is substantially located in a midplane passing between the two spinous processes AE. Thus, the implantation method is called a primarily dorsal approach one, to the extent that it involves a dorsal approach slightly eccentric with respect to the dorsal axis by the lateral distance DL.

This prior step of determining the reference point may be carried out well ahead for example through the use of a preoperative scanner, the preoperative scanner also allowing measuring the width of the targeted interspinous space and selecting a size of the implant 1 according to this width.

Afterwards, the surgeon performs an incision at the lateral distance DL with respect to the axis AC of the vertebral column CV, above the reference point.

In a first step illustrated in FIG. 11, the surgeon moves away the different elements such as tissues, muscles, ligaments, etc. by means of a spacer (not illustrated) and he inserts, via a dorsal approach, a positioning punch 6 forming a component of the implantation ancillary, until anchoring it on the reference point.

This positioning punch 6 is a slender and rectilinear rod having a tip-shaped distal end 61. This positioning punch 6 has a rectangular cross-section, without this shape being restrictive as the positioning punch 6 could also have a circular, square, polygonal cross-section or others. The tip-shaped distal end 61 is anchored on the reference point in the vertebra PE lateral portion PL.

This positioning punch 6 also has a proximal end 62, opposite to the distal end 61, and the positioning punch 6 is long enough for this proximal end 62 projecting from the back of the patient.

In a second step illustrated in FIG. 12, the surgeon inserts a primary support 7 by making it slide on the positioning punch 6, as schematized by the arrow GU; this primary support 7 being another component of the implantation ancillary.

This primary support 7 is in the form of a tubular and slender body, having a distal portion 71 and a proximal portion 72 opposite to each other. The distal portion 71 has a distal face 710 directed towards the vertebra when in place, from which project several spikes 711 forming anchoring reliefs configured to enable anchorage on the vertebra VE lateral portion PL. The proximal portion 72 has a proximal face 720 directed outwardly, opposite to the distal face 710.

The primary support 7 has a distal hole 73 (shown in FIG. 13) opening into its distal face 710 and also has a proximal hole 730 (shown in FIG. 12) opening into its proximal face 720; these two holes 73, 730 may include two holes that are blind or open through into each other.

This primary support 7 is longer than the positioning punch 6 and the distal hole 73 is substantially longer than the positioning punch 6. Thus, the positioning punch 6 is shaped so as to slidably guide the primary support 7 longitudinally by insertion of the positioning punch 6 inside the distal hole 73.

The primary support 7 is introduced from outside at the level of the proximal end 62, by fitting at the level of the proximal face 720, and then the primary support 7 slides along the positioning punch 6 (as schematized by the arrow GU) until the spikes 711 come into contact with the vertebra VE lateral portion PL.

The distal portion 71 of the primary support 7 widens in the direction of the distal face 710 and it has a front face 712, directed in the direction of the spinous processes AE, having a curved and concave shape, from which projects a concave arcuate rail 74, having a dovetail cross-section.

In a third step illustrated in FIG. 12, the surgeon couples a holding grip 75 on the proximal portion 72 of the primary support 7, and more specifically fixes the holding grip 75 on the proximal face 720 of the primary support 7.

It should be noted that the holding grip 75 could, in a preferred variant, be already coupled to the primary support 7 during the above-described second step, so that the holding grip 75 is already fastened to the primary support 7 before the insertion of this primary support 7 for the surgeon to be able to properly hold the primary support 7/holding grip 75 set and make it slide on the positioning punch 6.

This holding grip 7 comprises a main body 76 prolonged on one side by a gripping head 77 and, on another side, by a fitting pin 78 adapted to fit into the proximal hole 730 of the primary support 7 for coupling. The gripping head 77 is provided with two lateral wings 770 enabling a manual gripping of the holding grip 7.

Advantageously, the gripping head 77 is mounted movable in rotation over 90 degrees on the main body 76, with a locking system allowing locking the gripping head 77 in a first position and in a second position after having turned by 90 degrees. Also, this locking system comprises an unlock button 771 located on the gripping head 77, at the middle and in line with the main body 70 between the two lateral wings 770, and which allows unlocking the rotation of the gripping head 77 to switch from the first position into the second position and vice versa.

Afterwards, the surgeon will exert, thanks to the holding grip 75, a push on the primary support 7 in order to anchor it into the vertebra VE lateral portion PL, by exerting a pushing force, and possibly an impaction force, preferably repeated, on the griping head 77 to ram the primary support 7.

In a fourth step illustrated in FIG. 14, the surgeon inserts an implantation spindle 8, another component of the implantation ancillary. As it will be explained later on, such an implantation spindle 8 could be pre-mounted on the primary support 7 so that the surgeon inserts the primary support 7/holding grip 75/implantation spindle 8 set together, in one single step.

This implantation spindle 8 has a distal end portion 81 which extends up to a free and tip-shaped distal end 810, and it also has a proximal end portion 82 which extends the distal end portion 81 up to a free proximal end 820.

As shown in FIGS. 16 and 17, the tip-shaped free distal end 810 has a tip angle smaller than 90 degrees, and preferably smaller than 45 degrees.

The distal end portion 81 has a curved shape and a curved guide rail is provided on this distal end portion 81. This guide rail 83 has a shape complementary with the anterior groove 5 of the implant 1, and has the same radius of curvature RC, to enable a sliding guidance of the implant 1 as described later on. The proximal end portion 82 has a rectilinear shape.

The curvature of the distal end portion 81 is such that this distal end portion 81 extends, with respect to the proximal end portion 82, over an angular sector in the range of 90 degrees, more or less 30 degrees. In particular, the distal end portion 81 is curved in a circular arc over the given radius of curvature RC over such an angular sector in the range of 90 degrees.

The implantation spindle 8 has a square or rectangular cross-section, over the entirety of its length starting from its distal end 810 up to its proximal end 820. The implantation spindle 8 has:
 an anterior face 87 directed towards the primary support 7 when in place;
 a posterior face 84 opposite to the anterior face 87 and directed towards the implant 1 during the insertion thereof;
 two lateral faces 85 opposite to each other, respectively an upper face and a lower face.

The guide rail 83 is made in the form of two notches 830 formed in the respective lateral faces 85 at the level of the distal end portion 81. The guide rail 83 extends up to the distal end 810, in other words the notches 830 extend up to the distal end 810.

This guide rail 83 is curved in a circular arc over the given radius of curvature RC over an angular sector in the range of 90 degrees, more or less 30 degrees.

Moreover, the guide rail 83 is prolonged, from the distal end portion 81, by a longitudinal rail 89 formed on the proximal end portion 82 and extending up to the proximal end 820. This longitudinal rail 89 is a rectilinear rail and it is formed by two notches 890 formed in the respective lateral faces 85 at the level of the proximal portion 82 and extending the notches 830.

Thus, the implantation spindle 8 successively has an arcuate guide rail 83 along the distal end portion 81, also arcuate, and a rectilinear longitudinal rail 89 along the proximal end portion 82, also rectilinear.

Moreover, the distal end portion 81 has an arcuate slide 86 formed on the anterior face 87. This arcuate slide 86 extends up to the distal end 810 over an angular sector in the range of 90 degrees, more or less 30 degrees.

In particular, this arcuate slide 86 extends only over the distal end portion 81 and stops at the beginning of the proximal end portion 82. In a non-illustrated variant, this arcuate slide 86 extends over the distal end portion 81 and extends over the proximal end portion 82 up to the proximal end 820, for example, if during manufacture thereof, the implantation spindle 8 is first extruded and then curved.

This arcuate slide 86 has a shape complementary with the arcuate rail 74 provided on the front face 712 of the distal portion 71 of the primary support 7. This arcuate rail 74 and this arcuate slide 86 respectively form a first pivot guide means and a second pivot guide means adapted to cooperate together so as to pivotably guide the implantation spindle 8 during an insertion of its distal end portion 81 between the two spinous processes AE.

Also, in the fourth step of inserting the implantation spindle 8, as shown in FIG. 14, the implantation spindle 8 is inserted with its proximal end portion 82 substantially perpendicular to the primary support 7, and with its distal end portion 81 which has its distal end 810 which points towards the front face 712 of the distal portion 71 of the primary support 7, until the arcuate slide 86 engages with the arcuate rail 74.

Although not illustrated, it is advantageous that the implantation spindle 8 is already pre-mounted on the primary support 7 in the non-tilted position (as shown in FIG. 14), so that the surgeon inserts the primary support 7/holding grip 75/implantation spindle 8 set together (in one single introduction step), by making the whole slide on the positioning punch 6 through an action on the holding grip 75.

However, should the surgeon have to move away more tissues in the axis of the lateral approach (axis AL of the implant 1) for example by means of a scraping tool such as a scraper, then in this case the implantation spindle 8 would not be mounted directly on the primary support 7 to facilitate spreading of the tissues.

In a fifth step illustrated in FIG. 18, the surgeon makes the implantation spindle 8 pivot (or tilt) relative to the anchored and static primary support 7, as schematized by the arrow PG, until the proximal end portion 82 is pressed against the primary support 7 and the distal end portion 81 extends partially between the two spinous processes AE.

As explained hereinabove, this pivoting of the implantation spindle 8 is carried out thanks to the cooperation between the arcuate slide 86 and the arcuate rail 74. The pivoting of the implantation spindle 8 is performed over an angle in the range of 90 degrees.

The dovetail complementary shapes of the arcuate slide 86 and the arcuate rail 74 allow maintaining the contact between the arcuate slide 86 and the arcuate rail 74 without any risk of detachment of the distal end portion 81 of the implantation spindle 8 off the primary support 7.

In a sixth step illustrated in FIG. 22, the surgeon inserts a set comprising an ancillary-holder 9 and an impactor 13; the ancillary-holder 9 and the impactor 13 being also components of the implantation ancillary.

Referring to FIGS. 19 and 20, the ancillary-holder 9 has a distal portion 91 and a proximal portion 92 opposite to each other, linked by two parallel rods 93.

The distal portion 91 is provided with support means shaped so as to support the implant 1, where these support means comprise two support elements 94, 95 having inner faces 940, 950 facing each other and respectively provided with protrusions 941, 951.

These protrusions 941, 951 are shaped at least partially in a circular arc centered on the transverse axis AT and they form pivot means complementary with the recesses 23 formed in the rear portion 2 of the implant 1 to enable a relative pivoting of the implant 1 on this implant-holder 9 around the transverse axis AT.

As shown in FIG. 21, each protrusion 941, 951 is in the form of a protrusion shaped in a circular arc over an angular sector smaller than 180 degrees, such as for example and without limitation an angular sector comprised between 20 and 175 degrees.

Moreover, the support elements 94, 95 also have respective arcuate faces 943, 953, which border the respective inner faces 940, 950, and which are shaped in a circular arc centered on the transverse axis AT, wherein these two arcuate faces 943, 953 are intended to conform to the rounded shape of the rear end 20 of the implant 1 so as to allow holding the implant 1 in place and also to allow transmitting a push on the implant 1 during the insertion thereof.

Thus, the protrusions 941, 951 carry the implant 1 which has its rear portion 2 wedged between the inner faces 940, 950 with the protrusions 941, 951 fitted in the recesses 23, and which also has its rounded rear end 20 bearing against the arcuate faces 943, 953.

The two rods 93 have distal ends fastened on the respective support elements 94, 95. Moreover, the two support elements 94, 95 are detachably attached to one another and, to this end, these support elements 94, 95 are provided with removable attachment means so that the two support elements 94, 95 can be configured between:
  an attached configuration (to the left in FIG. 21) to allow supporting the implant 1, and
  a detached configuration (to the right in FIG. 21) to allow releasing the implant 1 and thus removing the implant-holder 9 as described later on.

More specifically and as shown in FIG. 21, the removable attachment means are formed by an upper slide 942 and by an upper rail 952 which are provided on the respective support elements 94, 95, and vice versa.

This upper slide 942 and this upper rail 952 are both arcuate and with dovetail complementary shapes, and they extend between an anterior face and a posterior face of the distal portion 91; the anterior face being directed towards the implantation spindle 8 when in place and the posterior face, opposite to the anterior face, being directed towards the spinous processes AE when in place.

This upper slide 942 and this upper rail 952 form pivot guide means adapted to cooperate together so as to pivotably guide a support element 94 relative to the other support element 95, around the transverse axis AT.

In the attached configuration, the upper rail 952 is integrally nested or received within the upper slide 942 and the two support elements 94, 95 are attached to one another and can support the implant 1 on their protrusions 941, 951.

Moreover, it should be noted that the distal ends of the rods 93 have respective terminations 930 which project from the respective support elements 94, 95, and these terminations 930 are intended to bear against the rear faces 241 of the respective blocking plates 24 of the implant 1 (as shown in FIG. 23), in order to hold the implant 1 in place and also to allow transmitting a push on the implant 1 during the insertion thereof.

To switch from the attached configuration into the detached configuration, all it needs is to make one of the support elements 94, 95 pivot around the transverse axis AT, which does not hinder the implant 1, until the upper rail 952 completely comes out of the upper slide 942.

The anterior face of the distal portion 91 of the implant-holder 9 has a groove 96 to partially receive the implantation spindle 8, as shown in FIG. 23. This groove 96 being formed by two half-grooves facing each other and formed in the respective support elements 94, 95.

Each of the two rods 93 has a circular cross-section, without this shape being restrictive as each rod 93 could also have a rectangular, square, polygonal cross-section or others.

The two rods 93 have proximal ends, opposite to their distal ends, which are removably fastened on the proximal portion 92. This proximal portion 92 is in the form of an integral body which links the proximal ends of the two rods 93 to each other, and this proximal portion 92 could be detached from the proximal ends of the two rods 93 where necessary, as described later on.

The impactor 13 comprises an impaction rod 14 provided with a distal end fastened on the proximal portion 92, between the proximal ends of the two rods 93. This impaction rod 14 is also provided with a proximal end, opposite to the distal end, and on which is fastened a grip 15 formed by two lateral wings enabling a manual gripping of the impactor 13. The impactor 13 further comprises an impaction sleeve 16 slidably mounted around the impaction rod 14, between the grip 15 and the proximal portion 92 of the implant-holder 9.

Thus, thanks to the impactor 13, the surgeon can exert a push on the implant-holder 9, and therefore on the implant 1, in order to position the implant 1 between the two spinous processes AE, by exerting a pushing force, preferably repeatedly, which includes holding with one hand the grip 15 and exerting with the other hand a sliding movement of the impaction grip 16 so that it impacts on the proximal portion 92; this impaction force being then transmitted through the rods 93 up to the support elements 94, 95, and finally through the terminations 930 and the arcuate faces 943, 953 up to the implant.

At the beginning of the sixth step, the implant 1 is engaged on the longitudinal rail 89 of the implantation spindle 8, along its posterior face 84, at the level of its proximal end 820, while engaging its anterior groove 5 by its front mouth 55 on the longitudinal rail 89, and with its front end 40 which points in the direction of the vertebra VE lateral portion PL.

More specifically, the retaining lips 53 of the anterior groove 5 are fitted inside the notches 890 formed in the respective lateral faces 85 of the implantation spindle 8. The retaining lips 53 allow maintaining contact between the anterior groove 5 and the longitudinal rail 89 without any risk of detachment of the implant 1 off the implantation spindle 8.

It should be noted that, because of the arcuate shape of the anterior groove 5 and its retaining lips 53, the longitudinal rail 86 is wider than the arcuate guide rail 83. In other words, and as shown in FIG. 17, the notches 890 of the longitudinal rail 89 have a width LR, and they are prolonged by the notches 830 which have a width LC smaller than LR.

More specifically, and as shown in FIG. 17, each notch 890 of the longitudinal rail 89 is delimited at the level of the posterior face 84 by a notch edge 891 having a thickness ER. Similarly, and as shown in FIG. 17, each notch 830 of the arcuate guide rail 83 is delimited at the level of the posterior face 84 by a notch edge 831 having a thickness EC, where EC is larger than ER, and where LR+ER=LC+EC. Thus, each notch edge 891 is prolonged by the corresponding notch edge 831, with a widening of one towards the other.

It should be noted that the thickness ER is substantially equivalent to the intermediate height HI of the anterior groove 5 (cf. FIG. 5), and the width LR is substantially equivalent to the overall height HG of the retaining lips 53 of the anterior groove 5 (cf. FIG. 5), so that the implant 1 could slide along a rectilinear path along the longitudinal rail 89, with the retaining lips 53 of its anterior groove 5 which slide in the notches 890; the notch edges 891 sliding, in turn, in the longitudinal interstice defined by this intermediate height HI.

Moreover, the thickness EC is substantially equivalent to the groove height HR of the anterior groove 5 (cf. FIG. 5), and the width LC is substantially equivalent to the lip height HL of the retaining lips 53 of the anterior groove 5 (cf. FIG. 5), so that the implant 1 could slide along an arcuate path (centered on the center of curvature of the anterior face 11 of the implant 1 which coincides with the center of curvature of the guide rail 83), with the retaining lips 53 of its anterior groove 5 which slide in the notches 830.

During the sixth step, the surgeon therefore pushes on the implant-holder 9, by means of the impactor 13, to make the implant-holder 9 and the implant 1 descend along the longitudinal rail 89 and therefore along the proximal end portion 82 of the implantation spindle 8, as schematized by the arrow EN in FIG. 22, until the anterior groove 5 reaches the arcuate guide rail 83.

It should be noted that the surgeon has made the gripping head 77 of the holding grip 75 pivot by 90 degrees beforehand, after having pushed the unlock button 771, for the gripping head 77 to be able to pass between the two rods 93, as shown in FIG. 22.

In a seventh step illustrated in FIGS. 25 to 28, the surgeon continues pushing on the implant-holder 9, by means of the impactor 13, to make the implant 1 slide along the arcuate guide rail 83 (facing the posterior face 84) of the distal end portion 81, and therefore along a curvilinear path which makes the implant 1 pivot over an angle in the range of 90 degrees and move in the direction of the interspinous space between the two spinous processes AE, until the implant 1 reaches a final position between the two spinous processes AE, as shown in FIGS. 27 and 28.

In this seventh step, the retaining lips 53 of the anterior groove 5 are fitted inside the notches 830, after having passed through the notches 890. These retaining lips 53 allow maintaining contact between the anterior groove 5 and the guide rail 83 without any risk of detachment of the implant 1 off the implantation spindle 8.

During this curvilinear displacement of the implant 1, this implant 1 pivots relative to the implant-holder 9, thanks to the protrusions 941, 951 which cooperate with the recesses 23, and switches from an initial orientation substantially parallel to the primary support 7 into a final orientation substantially perpendicular to the primary support 7.

Thus, the implant-holder 9 pivots (or tilts) concomitantly with sliding of the implant 1, as schematized by the arrow BA in FIG. 25, with the proximal portion 92 which passes above the holding grip 75. During this insertion, the streamlined shape of the front portion 4 of the implant 1 allows spreading the two spinous processes AE, to fit its central portion 3 between the two spinous processes AE.

Once the implant 1 is in place, the surgeon can perform a control radio. Where needed, he can remove the implant 1 by pulling on the impaction head 15 to make the implant-holder 9 and therefore the implant 1 rise. If the implant is properly placed, the surgeon continues on to the eight step described hereinbelow.

In an eighth step illustrated in FIG. 29, the surgeon removes the impactor 13 off the implant-holder 9, and for this purpose, he detaches the proximal portion 92 of the rods 93 and he pulls on the grip 15 to remove this impactor 13.

In a ninth step illustrated in FIG. 30, the surgeon unlocks the implant-holder 9 by making its two support elements 94, 95 switch into the detached configuration.

For this purpose, the surgeon on the rods 93 to make a support element 94 pivot relative to the other support element 95, as schematized by the arrow MA in FIGS. 30 and 31, until the upper rail 952 completely comes out of the upper slide 942, as shown in FIG. 31.

Thus, the surgeon continues by completely removing the implant-holder 9 which is detached off the implant 1, by pulling on one rod 93 which carries with it the support element 94 attached thereto, and afterwards by pulling on the other rod 93 which carries with it the other support element 95 attached thereto.

In a tenth step illustrated in FIG. 32, the surgeon removes the implantation spindle 8, and for this purpose he makes the implantation spindle 8 pivot (or tilt) relative to the anchored and static primary support 7, as schematized by the arrow BR, to bring the proximal end portion 82 away from the primary support 7 and make the distal end portion 81 comes out of the anterior groove 5 (by its rear mouth 54) of the implant 1.

This pivoting of the implantation spindle 8 is performed over an angle in the range of 90 degrees, with a rotation opposite to that performed upon its implantation on the primary support 7.

Thus, the surgeon continues by completely removing the implantation spindle 8, then he pulls on the primary support 7, by means of the gripping head 77 of the holding grip 75, to remove the primary support 7, and finally the surgeon removes the positioning punch 6.

At this level, only the implant 1 is in place between the spinous processes AE, as illustrated in FIGS. 8 to 10, and the surgeon can finish the intervention, in particular by removing the spreader and by closing the incision.

The invention claimed is:

1. An interspinous vertebral implant including an implant body extending along a longitudinal axis and comprising successively along said longitudinal axis:
    a rear portion having a rear end,
    a central portion shaped so as to extend between two spinous processes of two adjacent vertebrae, said central portion extending the rear portion, and
    a front portion extending the central portion, opposite to the rear portion, while tapering up to a front end of streamlined shape,
    wherein said implant body has:
    an anterior face intended to be directed towards the vertebrae,
    a guide channel formed in the implant body from its rear end up to its front end, said guide channel being shaped so as to receive at least one portion of an implantation spindle of an implantation ancillary;
    wherein the guide channel extends from the rear end up to the front end along a curvilinear direction, said guide channel being formed in the anterior face so that said guide channel forms a continuous anterior groove in the anterior face of the implant body from the rear end to the front end, so as to continuously open into the anterior face, and having a curvilinear shape along an entire length of the guide channel and continuously opening outside into said anterior face of the implant body,
    wherein the anterior groove has a convex shape having a given radius of curvature, with a center of curvature located facing a posterior face of the implant body, opposite to the anterior face, and the anterior face has a convex shape having the radius of curvature,
    and wherein the anterior groove is internally delimited by a bottom wall offset in depth with respect to the anterior face, said bottom wall having a convex shape, and the anterior groove is externally delimited by retaining lips with a convex shape having the radius of curvature, said retaining lips being disposed facing the bottom wall and extending facing each other so as to delimit a narrow space in comparison with the interior of the anterior groove.

2. The interspinous vertebral implant according to claim 1, wherein the implant body is not articulated, so that, in a rest position as well as in an implanted position, the anterior groove is curvilinear shaped along the same curvature.

3. The interspinous vertebral implant according to claim 1, wherein the radius of curvature is comprised between 20 and 300 millimeters.

4. The interspinous vertebral implant according to claim 1, wherein the rear portion has pivot means around a transverse axis extending transversely with respect to the longitudinal axis to enable a pivoting of said implant body relative to complementary pivot means provided on an implant-holder of the implantation ancillary.

5. The interspinous vertebral implant according to claim 4, wherein the rear portion has two opposite lateral faces, respectively an upper face and a lower face, and the pivot means are provided on said opposite lateral faces in the form of recesses or of protrusions shaped at least partially in a circular arc centered on the transverse axis.

6. The interspinous vertebral implant according to claim 1, wherein the front portion comprises facets directly connected to each other by sharp edges converging towards the front end tapering into a tip.

7. The interspinous vertebral implant according to claim 1, wherein the rear portion comprises, at an interface with the central portion, at least one blocking plate projecting on a lower side of the rear portion or on an upper side of the rear portion, opposite to the lower side.

8. The interspinous vertebral implant according to claim 7, wherein the rear portion comprises, at the interface with the central portion, a blocking plate projecting on the lower side of the rear portion and another blocking plate projecting on the upper side of the rear portion.

9. The interspinous vertebral implant according to claim 7, wherein the at least one blocking plate extends from the lower side or the upper side of the rear portion in a plane orthogonal to the longitudinal axis or inclined with respect to the longitudinal axis by an angle comprised between 60 and 120 degrees.

10. The interspinous vertebral implant according to claim 7, wherein the at least one blocking plate has a front face directed in the direction of the front end and on which is provided at least one anchoring relief configured to enable anchorage on a spinous process.

11. The interspinous vertebral implant according to claim 1, wherein the central portion has two opposite lateral faces, respectively an upper face and a lower face, which are concave so as to define two recessed lateral faces adapted to fit between the two spinous processes.

12. The interspinous vertebral implant according to claim 1, wherein the rear portion comprises, at an interface with the central portion, a first blocking plate projecting on a lower side of the rear portion and a second blocking plate projecting on an upper side of the rear portion, opposite to the lower side, wherein the two blocking plates are symmetrical with respect to a midplane containing the longitudinal axis and the anterior groove extends in the midplane and is symmetrical with respect to the midplane.

13. A set comprising an interspinous vertebral implant according to claim 1, and an implantation ancillary, intended for guidance and positioning of the interspinous vertebral implant between two spinous processes of two adjacent vertebrae, the implantation ancillary comprising:
    an implant-holder having a distal portion and a proximal portion opposite to each other, said distal portion being provided to support said interspinous vertebral implant; and
    an implantation spindle having a distal end portion which extends up to a free distal end of tip shape, said distal end portion having a curved shape and on which is provided a curved guide rail with a shape complementary with the anterior groove of the interspinous vertebral implant to enable a sliding guidance of said interspinous vertebral implant along a posterior face of said distal end portion by fitting of the guide rail inside the anterior groove, said guide rail extending up to the free distal end.

* * * * *